United States Patent
Chakravarthy et al.

(10) Patent No.: US 11,504,048 B2
(45) Date of Patent: Nov. 22, 2022

(54) TRIGGERING ARRHYTHMIA EPISODES FOR HEART FAILURE AND CHRONOTROPIC INCOMPETENCE DIAGNOSIS AND MONITORING

(71) Applicant: Medtronic Monitoring, Inc., San Jose, CA (US)

(72) Inventors: Niranjan Chakravarthy, Singapore (SG); Rodolphe Katra, Blaine, MN (US)

(73) Assignee: Medtronic Monitoring, Inc., San Jose, CA (US)

(*) Notice: Subject to any disclaimer, the term of this patent is extended or adjusted under 35 U.S.C. 154(b) by 217 days.

(21) Appl. No.: 16/897,912

(22) Filed: Jun. 10, 2020

(65) Prior Publication Data
US 2021/0386312 A1 Dec. 16, 2021

(51) Int. Cl.
| A61B 5/363 | (2021.01) |
| A61B 5/316 | (2021.01) |
| A61B 5/0245 | (2006.01) |
| A61B 5/11 | (2006.01) |
| A61B 5/00 | (2006.01) |

(52) U.S. Cl.
CPC .......... *A61B 5/363* (2021.01); *A61B 5/02455* (2013.01); *A61B 5/1118* (2013.01); *A61B 5/316* (2021.01); *A61B 5/725* (2013.01); *A61B 5/7207* (2013.01); *A61B 2562/0219* (2013.01)

(58) Field of Classification Search
CPC .... A61B 2560/0209; A61B 2562/0219; A61B 5/02455; A61B 5/1118; A61B 5/316; A61B 5/363; A61B 5/4836; A61B 5/686; A61B 5/7207; A61B 5/725; A61B 5/7285; A61N 1/3621; A61N 1/36542; A61N 1/37247; A61N 1/37258; A61N 1/37282
See application file for complete search history.

(56) References Cited

U.S. PATENT DOCUMENTS

| 5,518,001 A | 5/1996 | Snell |
| 6,730,027 B2 | 5/2004 | Iliff |
| 7,008,378 B2 | 3/2006 | Dean |

(Continued)

FOREIGN PATENT DOCUMENTS

| JP | 5946572 A | 7/2016 |

OTHER PUBLICATIONS

International Search Report and Written Opinion of International Application No. PCT/US2021/034141, dated Sep. 16, 2021, 13 pp..

*Primary Examiner* — George Manuel
(74) *Attorney, Agent, or Firm* — Shumaker & Sieffert, P.A.

(57) ABSTRACT

Techniques are disclosed for detecting arrhythmia episodes for a patient. A medical device may receive one or more sensor values indicative of motion of a patient. The medical device may determine, based at least in part on the one or more sensor values, an activity level of the patient. The medical device may determine a heart rate threshold for triggering detection of an arrhythmia episode based at least in part on the activity level of the patient. The medical device may determine whether to trigger detection of the arrhythmia episode for the patient based at least in part on comparing a heart rate of the patient with the heart rate threshold. The medical device may, in response to triggering detection of the arrhythmia episode, collect information associated with the arrhythmia episode.

18 Claims, 8 Drawing Sheets

(56) References Cited

U.S. PATENT DOCUMENTS

| | | |
|---|---|---|
| 7,149,756 B1 | 12/2006 | Schmitt et al. |
| 7,204,805 B2 | 4/2007 | Dean |
| 8,915,869 B2 | 12/2014 | Wekell |
| 8,965,818 B2 | 2/2015 | Zillner et al. |
| 9,002,769 B2 | 4/2015 | Oberkampf et al. |
| 9,977,875 B2 | 5/2018 | Lo et al. |
| 2003/0144829 A1 | 7/2003 | Geatz et al. |
| 2005/0256545 A1* | 11/2005 | Koh .................. A61B 5/0245 607/17 |
| 2007/0142732 A1 | 6/2007 | Brockway et al. |
| 2009/0259134 A1 | 10/2009 | Levine |
| 2010/0010832 A1 | 1/2010 | Boute et al. |
| 2015/0332020 A1 | 11/2015 | Lo et al. |
| 2016/0089089 A1 | 3/2016 | Kakkar et al. |
| 2017/0087371 A1 | 3/2017 | Freeman et al. |
| 2018/0113991 A1 | 4/2018 | Davidson |
| 2018/0116598 A1 | 5/2018 | Lee et al. |
| 2018/0132793 A1 | 5/2018 | Katra et al. |
| 2019/0008384 A1 | 1/2019 | Brisben et al. |
| 2019/0343415 A1 | 11/2019 | Saha et al. |

\* cited by examiner

TRIGGERING ARRHYTHMIA EPISODES FOR HEART FAILURE AND CHRONOTROPIC INCOMPETENCE DIAGNOSIS AND MONITORING

FIELD

This disclosure generally relates to medical devices and, more particularly, to medical devices configured to detect arrhythmia episodes.

BACKGROUND

Arrhythmia diagnosis systems, such as SEEQ™ Mobile Cardiac Telemetry (MCT) system, AVIVO™ Mobile Patient Management (MPM) system, or the Reveal LINQ Insertable Cardiac Monitor, each of which was or is available from Medtronic, Inc., of Minneapolis, Minn., may be able to perform cardiac monitoring of patients for the occurrence of arrhythmia episodes. Such systems may, upon detecting the occurrence of an arrhythmia episode, capture information associated with the arrhythmia episode, such as cardiac electrogram data of the patient during the arrhythmia episode and may send that data to a remote system for review by, e.g., a physician.

An arrhythmia diagnosis system may detect the occurrence of arrhythmia episodes based on the heart rate of the patient. For example, the system may trigger tachyarrhythmia episodes for the patient when the heart rate of the patient exceeds a preset threshold, such as 120 beats per minute (BPM). Similarly, the system may trigger bradyarrhythmia episodes for the patient when the heart rate of the patient falls below a preset threshold, such as 40 BPM.

SUMMARY

In accordance with the techniques of the disclosure, a medical device system is set forth herein that is able to capture diagnostically-relevant arrhythmia episodes, the detection of which are triggered based on the activity state of the patient. More specifically, a medical device system as described herein may derive the patient's activity level via use of a wearable device worn by the patient or an implantable medical device (IMD) implanted within the patient that includes one or more activity sensors, such as an accelerometer, and may capture certain diagnostically relevant episodes when the activity level of the patient satisfies one or more criteria. In some examples, the medical device system determines the heart rate thresholds for triggering detection one or more arrhythmia episodes for the patient based on the patient's activity level.

In certain patient populations, such as heart failure patients and chronotropic incompetence patients, it may not be diagnostically sufficient to trigger detection of arrhythmia episodes based on preset heart rate thresholds that are the same as for other populations of patients. For example, for heart failure patients, a resting heart rate of over a certain threshold, e.g., 80 BPM, may indicate that the heart failure status of the patient is worsening. However, if the tachycardia threshold for the medical device system is preset to a typically tachyarrhythmia threshold, e.g., 120 BPM, the medical device system may not capture tachyarrhythmia episodes when the heart rate of the patient is between 80 BPM and 120 BPM, even though such tachyarrhythmia episodes may be diagnostically relevant for the heart failure patient.

Similarly, for chronotropic incompetence patients, heart rates not exceeding a certain threshold, e.g., 64 BPM for a 60 year old patient during moderate activity, may be an indication of chronotropic incompetence for the patient. However, if the bradycardia threshold for the medical device system is preset to a typical bradyarrhythmia threshold, e.g., 40 BPM, the medical device system may not capture bradyarrhythmia episodes when the heart rate of the patient is between 40 BPM and 64 BPM, even though such bradyarrhythmia episodes may be diagnostically relevant for the chronotropic incompetence patient.

Lowering the tachycardia threshold at all times, such as from 120 BPM to 80 BPM, or increasing the bradycardia threshold at all times, such as from 40 BPM to 64 BPM, may not provide a high diagnostic yield for other arrhythmia monitoring applications, e.g., general mobile cardiac telemetry or Holter monitoring, and/or other patients. Further, because users such as clinicians or physicians may proactively review triggered tachyarrhythmia episodes and bradyarrhythmia episodes to notify prescribing physicians to take urgent action in near real-time, lowering the tachycardia and bradycardia thresholds at all times may substantially increase the number of times the medical device system may trigger tachyarrhythmia episodes and bradyarrhythmia episodes, thereby increasing the review burden and potentially making untenable the review process for reviewing such episodes and notifying prescribing physicians. In addition, substantially increasing the number of times the medical device system may trigger tachyarrhythmia and bradyarrhythmia episodes may decrease the battery life of the medical devices in the medical device system and may increase the memory usage of the medical devices in the medical device system.

In accordance with aspects of the present disclosure, instead of using preset tachycardia and bradycardia thresholds at all times for determining whether to trigger detection of tachyarrhythmia episodes and bradyarrhythmia episodes, a medical device system may adaptively adjust or otherwise determine tachycardia and bradycardia thresholds for a patient based at least in part on the activity level of the patient. Specifically, the medical device system may include a wearable device worn by the patient or an IMD implanted in the patient that may include one or more sensors for sensing the motion of the patient. The medical device system may determine, based on the sensor values generated by the one or more sensors, the activity level of the patient and may correspondingly determine a tachycardia threshold and/or a bradycardia threshold for the patient based at least in part on the activity level of the patient.

In some examples, the medical device system may determine, based at least in part on the sensor values, whether the activity level of the patient is below a resting threshold for at least a specified duration of time. If the medical device system determines that the activity level of the patient is below a resting threshold for at least a specified duration of time, the medical device system may determine the tachycardia threshold for the patient, such as by lowering the tachycardia threshold from, e.g., 120 BPM to, e.g., 80 BPM. In some examples, if the medical device system determines that the patient is at least moderately active, the medical device system may determine the bradycardia threshold for the patient, such as by raising the bradycardia threshold.

The techniques of the disclosure may provide specific improvements to the field of cardiac arrhythmia detection by medical devices. For example, the techniques of the disclosure may enable medical device systems to capture diagnostically relevant arrhythmia episodes that may not be captured by medical devices that do not determine heart rate thresholds based on the activity level of the patient, thereby improving the functioning of cardiac arrhythmia detection and monitoring devices. Further, by adaptively determining the heart rate thresholds based on the activity level of the patient, the techniques of the disclosure may prevent medical device systems from substantially increasing the number of times the medical device system may trigger non diagnostically relevant tachyarrhythmia episodes and bradyarrhythmia episodes, such as may occur by lowering the tachycardia threshold for all times or by raising the bradycardia threshold for all times, thereby reducing the power consumed by the medical device system to capture such episodes.

A system of one or more computers and/or devices can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect is directed to a method. The method includes receiving, by processing circuitry, one or more sensor values indicative of motion of a patient. The method also includes determining, by the processing circuitry and based at least in part on the one or more sensor values, an activity level of the patient. The method also includes determining, by the processing circuitry, a heart rate threshold for triggering detection of an arrhythmia episode based at least in part on the activity level of the patient. The method also includes determining, by the processing circuitry, whether to trigger detection of the arrhythmia episode for the patient based at least in part on comparing a heart rate of the patient with the heart rate threshold. The method also includes in response to triggering detection of the arrhythmia episode, collecting, by the processing circuitry, information associated with the arrhythmia episode. Other examples of this aspect include corresponding computer systems, apparatus, and computer programs recorded on one or more computer storage devices, each configured to perform the actions of the methods.

One general aspect is directed to a medical device. The medical device includes memory. The medical device also includes processing circuitry operably coupled to the memory and configured to: receive one or more sensor values indicative of motion of a patient; determine, based at least in part on the one or more sensor values, an activity level of the patient; determine a heart rate threshold for triggering detection of an arrhythmia episode based at least in part on the activity level of the patient; determine whether to trigger detection of the arrhythmia episode for the patient based at least in part on comparing a heart rate of the patient with the heart rate threshold; and in response to triggering detection of the arrhythmia episode, collect information associated with the arrhythmia episode. Other examples of this aspect include corresponding computer systems, apparatus, and computer programs recorded on one or more computer storage devices, each configured to perform the actions of the methods.

One general aspect is directed to a non-transitory computer-readable medium. The non-transitory computer-readable medium may include instructions that, when executed by a processing circuitry of a medical device, cause the medical device to: receive one or more sensor values indicative of motion of a patient; determine, based at least in part on the one or more sensor values, an activity level of the patient; determine a heart rate threshold for triggering detection of an arrhythmia episode based at least in part on the activity level of the patient; determine whether to trigger detection of the arrhythmia episode for the patient based at least in part on comparing a heart rate of the patient with the heart rate threshold; and in response to triggering detection of the arrhythmia episode, collect information associated with the arrhythmia episode. Other examples of this aspect include corresponding computer systems, apparatus, and computer programs recorded on one or more computer storage devices, each configured to perform the actions of the methods.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Techniques are disclosed for adaptively adjusting thresholds for capturing diagnostically-relevant arrhythmia episodes based on the activity state of a patient. A medical device system may use one or more sensors to sense the motion of the patient and may determine, based on sensor values generated by the one or more sensors, an activity level of the patient. The medical device system may accordingly adjust one or more thresholds for triggering arrhythmia episodes for the patient based at least in part on the activity level of the patient.

Figure 1:
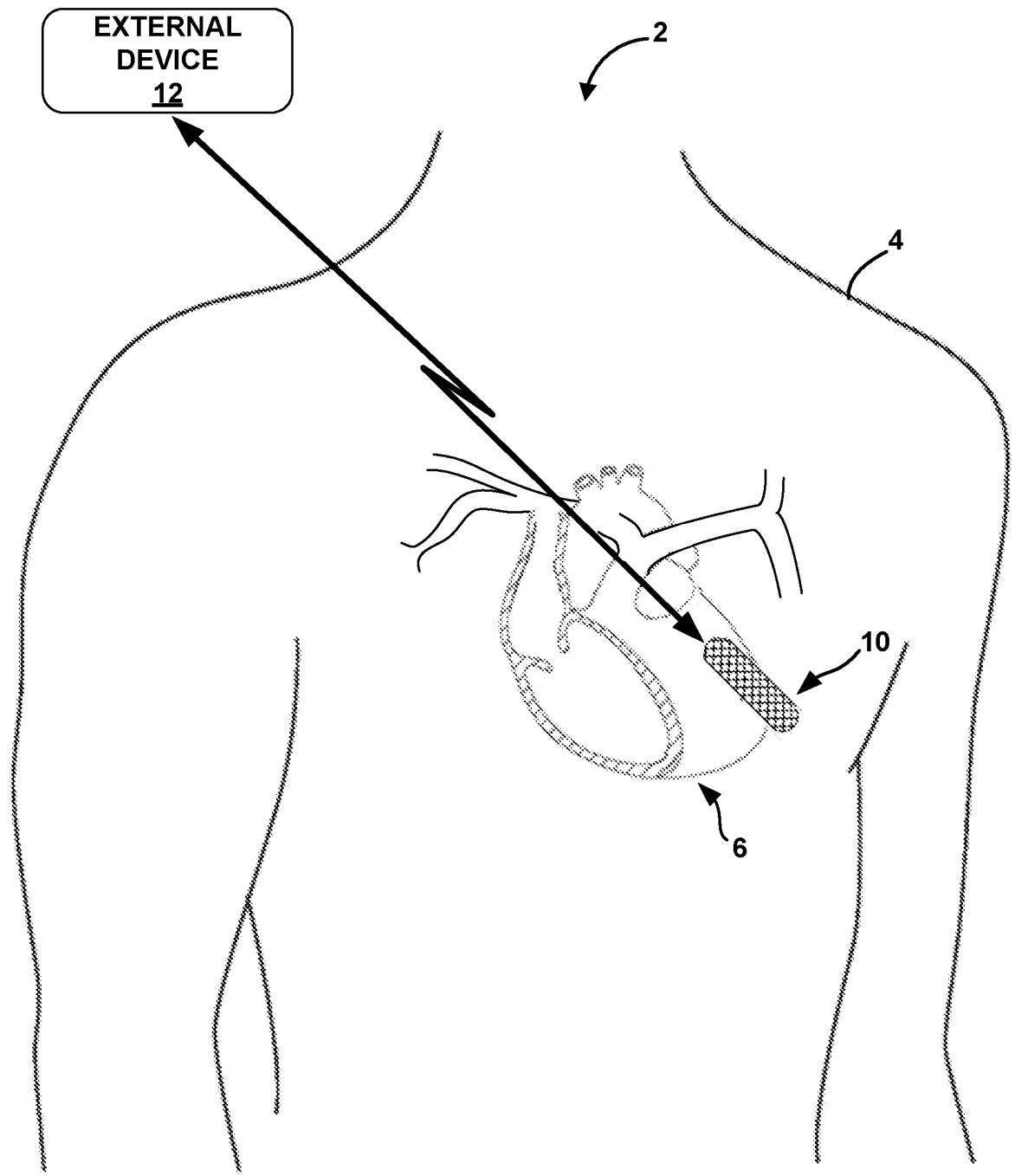
FIG. 1 illustrates the environment of an example of a medical device system in conjunction with a patient in accordance with the techniques of the disclosure.

FIG. 1 illustrates the environment of an example medical device system 2 in conjunction with a patient 4 and a heart 6, in accordance with an apparatus and method of certain examples described herein. The example techniques may be used with an IMD 10, which may be leadless and in wireless communication with external device 12, as illustrated in FIG. 1. In some examples, IMD 10 may be coupled to one or more leads. In some examples, IMD 10 may be implanted outside of a thoracic cavity of patient 4 (e.g., subcutaneously in the pectoral location illustrated in FIG. 1). IMD 10 may be positioned near the sternum near and/or just below the level of heart 6.

In some examples, IMD 10 may take the form of a Reveal LINQ™ Insertable Cardiac Monitor (ICM), available from Medtronic Inc., of Minneapolis, Minn. As discussed herein, the techniques of the disclosure may be performed by an implantable device, such as 1 MB 10.

In other examples, the techniques described herein may be performed by an external medical device such as external device 12 in addition to, or instead of IMD 10. Such an external medical device may be positioned externally to patient 4 (e.g., positioned on the skin of patient 4) and may carry out any or all of the functions described herein with respect to 1 MB 10. External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic Inc., of Minneapolis, Minn. External device 12 may, in some examples, comprise a programmer, an external monitor, or a mobile device, such as a mobile phone, a "smart" phone, a laptop, a tablet computer, a personal digital assistant (PDA), etc. In some examples, external device 12 is a wearable electronic device, such as the SEEQ™ Mobile Cardiac Telemetry (MCT) system that was available from Medtronic, Inc., the AVIVO™ Mobile Patient Management (MPM) system that was available from Medtronic, Inc., a Holter monitor, or a type of wearable "smart" electronic apparel, such as a "smart" watch, "smart" patch, or "smart" glasses. In some examples, system 2 may include one or more external devices 12 and need not include any IMDs.

In some examples, a user, such as a physician, technician, surgeon, electro-physiologist, or other clinician, may interact with external device 12 to retrieve physiological or diagnostic information from IMD 10. In some examples, a user, such as patient 4 or a clinician as described above, may also interact with external device 12 to program 1 MB 10, e.g., select or adjust values for operational parameters of IMD 10. In some examples, external device 12 acts as an access point to facilitate communication with 1 MB 10. In some examples, external device 12 may continually communicate with 1 MB 10 so that 1 MB 10 may continually send information sensed by 1 MB 10, such as heart rate data of patient 4, cardiac electrogram data of patient 4, and the like to external device 12.

A user, such as a physician, technician, surgeon, electro-physiologist, or other clinician, may interact with external device 12 to retrieve physiological or diagnostic information from IMD 10. A user may also interact with external device 12 to program IMD 10, e.g., select values for operational parameters of the 1 MB. External device 12 may include a processor configured to evaluate EGM and/or other sensed signals transmitted from IMD 10 to external device 12.

In any such examples, processing circuitry of medical device system 2, such as processing circuitry of external device 12, may transmit patient data, including cardiac electrogram data, for patient 4 to a remote computer (e.g., external device 12, or another device not depicted in FIG. 1). In some examples, processing circuitry of medical device system 2 may transmit a determination that patient 4 is undergoing an episode of cardiac arrhythmia such as an episode of bradycardia, tachycardia, atrial fibrillation, or ventricular fibrillation.

External device 12 may be a computing device (e.g., used in a home, ambulatory, clinic, or hospital setting) to communicate with IMD 10 via wireless telemetry. External device 12 may include or be coupled to a remote patient monitoring system, such as Carelink®, available from Medtronic, Inc., of Minneapolis, Minn. In some examples, external device 12 may receive data, alerts, patient physiological information, or other information from IMD 10.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule and/or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, WiFi, or medical implant communication service (MICS). In some examples, external device 12 may include a user interface configured to allow patient 4, a clinician, or another user to remotely interact with IMD 10.

In some such examples, external device 12, and/or any other device of medical device system 2, may be a wearable device (e.g., in the form of a necklace or other wearable item), that is operable to track the activity level of patient 4. Patient 4 may wear external device 12 on or near patient 4's chest, such as via a necklace that hangs external device 12 on or near patient 4's chest, via a strap that straps external device 12 on or near patient 4's chest, and the like. External device 12 being worn by patient 4 so that external device 12 is situated on or near patient 4's chest may enable external device 12 to potentially track the activity level of patient 4 in ways that may better reflect the actual activity level of patient 4 compared with devices that may be worn on patient 4's periphery, such as on patient 4's legs or hands.

Additional examples of the one or more other implanted or external devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, an external therapy delivery device such as an external pacing or electrical stimulation device, or a drug pump.

Communication circuitry of each of the devices of medical device system 2 (e.g., IMD 10 and external device 12) may enable the devices to communicate with one another. In addition, although one or more sensors (e.g., electrodes) are described herein as being positioned on a housing of IMD 10, in other examples, such sensors may be positioned on a housing of another device implanted in or external to patient 4. In such examples, one or more of the other devices may include processing circuitry configured to receive signals from the electrodes or other sensors on the respective devices and/or communication circuitry configured to transmit the signals from the electrodes or other sensors to another device (e.g., external device 12) or server.

In accordance with the techniques of the disclosure, medical device system 2 may monitor the heart rate of patient 4 for arrhythmia episodes, review the arrhythmia episodes of patient 4, and/or create arrhythmia reports based on the arrhythmia episodes. A medical device, such as IMD 10 or external device 12, may operate in one or more of a plurality of monitoring modes for monitoring the heart rate of patient 4 for arrhythmia episodes, and may adjust one or more heart rate thresholds for triggering an arrhythmia episode for patient 4 based at least in part on the activity level of patient 4. The medical device may, based at least in part on comparing the heart rate of patient 4 with the one or more heart rate thresholds, determine whether to trigger detection of an arrhythmia episode. If the medical device triggers an arrhythmia episode, the medical device may collect information related to the heart rate of patient 4 at the onset of the arrhythmia episode through the duration of the arrhythmia episode, and may send the collected information to a monitoring center or monitoring system for review.

In some examples, the plurality of monitoring modes may include a heart failure monitoring mode, a mobile cardiac telemetry/Holter-type arrhythmia monitoring mode, a functional chronotropic incompetence monitoring mode, and the like. As described above, external device 12 and/or IMD 10 may operate in one of the plurality of monitoring modes or may operate in two or more of the plurality of monitoring modes at the same time. Further, external device 12 and/or IMD 10 may be operable to switch between operating in different one or more of the plurality of monitoring modes. For example, a clinician may program external device 12 and/or IMD 10 to operate in one or more of the plurality of operating modes. In some examples, external device 12 and/or IMD 10 may automatically select an operating mode. In some examples, external device 12 and/or IMD 10 may turn on one or more of the operating modes all times, while in other examples, external device 12 and/or IMD 10 may automatically turn on one or more of the operating modes during specific intervals, such as turning on heart failure monitoring mode and/or chronotropic incompetence monitoring mode for patient 4 for a specified period of time post-hospitalization.

The arrhythmia threshold may be a threshold, in terms of BPM, for triggering detection of a tachyarrhythmia episode, a threshold for triggering detection of a bradyarrhythmia episode, and the like. In some examples, when the medical device is in a heart failure monitoring mode, the medical device may trigger a tachyarrhythmia episode if the heart rate of patient 4 rises above the tachycardia threshold that is lower than a tachycardia threshold in a mobile cardiac telemetry/Holter-type arrhythmia monitoring mode. In some examples, when the medical device is in a functional chronotropic incompetence monitoring mode, the medical device may trigger a bradyarrhythmia episode if the heart rate of patient 4 drops below the bradycardia threshold that is higher than a bradycardia threshold in a mobile cardiac telemetry/Holter-type arrhythmia monitoring mode.

To determine the activity level of patient 4, external device 12 and/or IMD 10 may include one or more sensors that are operable to sense the motion of external device 12 and/or IMD 10 and, by being worn by patient 4, such as in the case of external device 12, or by being implanted in patient 4, such as in the case of IMD 10, to sense the motion of patient 4. The one or more sensors may include one or more of: accelerometers, gyroscopes, and/or other motion sensors that may be able to sense one or more types of motion such as linear acceleration, rotation, steps, and the like and to output values indicative of the motion sensed by the one or more sensors. For example, external device 12 and/or IMD 10 may include an accelerometer that is operable to measure acceleration forces along multiple axis and to output accelerometer data, which may be values of the acceleration forces measured by the accelerometer, such as a three-axis accelerometer that measures acceleration forces along x, y, and z axis, and the accelerometer may output the values of the acceleration forces measured by the accelerometer along each of the axis.

External device 12 and/or IMD 10 may be operable to determine, based at least in part on the motion sensed by the one or more sensors, an activity level of patient 4. The activity level of patient 4 may, in some examples include any combination of an activity intensity, an activity type, a posture, an activity duration, and the like of patient 4. Because external device 12 is worn by patient 4 and because IMD 10 is implanted in patient 4, the motion sensed by the one or more sensors may correspond to the motion of patient 4, and the sensor values generated by the one or more sensors that correspond to the motion sensed by the one or more sensors may be indicative of the activity level of patient 4. External device 12 and/or IMD 10 may be operable to determine an activity level of patient 4 based at least in part on the sensor values generated by the one or more sensors using any suitable technique or algorithm.

External device 12 and/or IMD 10 may determine the threshold for triggering detection of an arrhythmia episode based at least in part on the activity level of patient 4 indicated by the one or more sensor values. Determining the threshold for triggering detection of an arrhythmia episode may include increasing the threshold from a preset value or decreasing the threshold from a preset value.

In some examples, external device 12 and/or IMD 10 may determine the tachycardia threshold for triggering detection of a tachyarrhythmia episode for patient 4 based at least in part on the activity level of patient 4. As described above, for heart failure patients, using the default tachycardia threshold for triggering detection of tachyarrhythmia episodes may cause external device 12 to miss detection of diagnostically relevant tachyarrhythmia episodes of patients when the patients are in a resting state.

As such, in some examples, when external device 12 and/or IMD 10 operates in a heart failure monitoring mode, external device 12 and/or IMD 10 may determine whether patient 4 is at rest. If external device 12 and/or IMD 10 determines that patient 4 is at rest, external device 12 and/or IMD 10 may adjust the tachycardia threshold for patient 4 by changing the tachycardia threshold from a preset tachycardia threshold. For example, if external device 12 and/or IMD 10 determines that patient 4 is at rest, external device 12 and/or IMD 10 may determine the tachycardia threshold for patient 4 by decreasing the tachycardia threshold from the preset tachycardia threshold to a resting tachycardia threshold, such as from a preset or default tachycardia threshold of 120 BPM to a resting tachycardia threshold of 80 BPM. If external device 12 and/or IMD 10 determines that patient 4 is no longer at rest, external device 12 may correspondingly change the tachycardia threshold from the resting tachycardia threshold back to the default tachycardia threshold.

In some examples, external device 12 and/or IMD 10 may, based on determining that patient 4 is at rest, determine a heart failure tachycardia threshold that is separate from a tachycardia threshold, so that external device 12 and/or IMD 10 may capture two types of arrhythmias: typical tachyarrhythmias and heart failure arrhythmias. In these examples, external device and/or IMD 10 may trigger a heart failure tachyarrhythmia episode in response to determining that the heart rate of patient 4 is above the heart failure tachycardia threshold.

To determine whether patient 4 is at rest, external device 12 and/or IMD 10 may determine the activity level of patient 4 from the sensor values and may determine whether the activity level of patient 4 determined from the sensor values is below a resting threshold for least a specified amount of time. By determining whether patient 4's activity level is below a resting threshold for at least a specified amount of time, external device 12 and/or IMD 10 may ensure that patient 4 is actually at rest and is not transitioning between activity states. If external device 12 and/or IMD 10 determines that the activity level of patient 4 is below the resting threshold for at least the specified amount of time, external device 12 and/or IMD 10 may determine that patient 4 is at rest and may therefore change the tachycardia threshold for patient 4 from a default tachycardia threshold to a resting tachycardia threshold. In some examples, external device 12 and/or IMD 10 may use patient 4's local time of day as an additional indicator to determine whether patient 4 is at rest. For example, if patient 4's local time of day is in the middle of the night, the patient 4's local time of day may indicate to external device 12 and/or IMD 10 that patient 4 is likely to be at rest.

In some examples, external device 12 and/or IMD 10 may adjust the bradycardia threshold for triggering detection of a bradyarrhythmia episode for patient 4 based at least in part on the activity level of patient 4. For chronotropic incompetence patients, using the default bradycardia threshold for triggering detection of bradyarrhythmia episodes may cause external device 12 and/or IMD 10 to miss detection of diagnostically relevant bradyarrhythmia episodes of patients when the patients are at least moderately active. Further, ensuring that patient 4 is at least moderately active may enable external device 12 and/or IMD 10 to more reliably capture bradyarrhythmia episodes for patient 4.

As such, in some examples, when external device 12 and/or IMD 10 operates in a functional chronotropic incompetence monitoring mode, external device 12 and/or IMD 10 may adjust the bradycardia threshold, such as by increasing the bradycardia threshold for patient 4 from a preset or default bradycardia threshold based at least in part on determining that patient 4 is at least moderately active. For example, if external device 12 and/or IMD 10 determines that patient 4 is moderately active, external device 12 and/or IMD 10 may adjust the bradycardia threshold for patient 4 by increasing the bradycardia threshold from the preset bradycardia threshold to a moderately active bradycardia threshold. If external device 12 and/or IMD 10 determines that patient 4 is highly active, external device 12 and/or IMD 10 may adjust the bradycardia threshold for patient 4 to a highly active bradycardia threshold. Because the bradycardia threshold is a function of the activity intensity of patient 4, the highly active bradycardia threshold may be higher than the moderately active bradycardia threshold. If external device 12 and/or IMD 10 determines that patient 4 is no longer at least moderately active, external device 12 and/or IMD 10 may correspondingly adjust the bradycardia threshold from the moderately active or highly active bradycardia threshold back to the default bradycardia threshold.

External device 12 and/or IMD 10 may monitor patient 4 to determine whether to trigger an arrhythmia episode based at least in part on comparing the heart rate of patient 4 with one or more heart rate thresholds. In some examples, IMD 10 may sense the heart rate of patient 4 and may send the sensed heart rate of patient 4 to external device 12. In some examples, external device 12 may sense the heart rate of patient 4 via one or more heart rate sensors.

External device 12 and/or IMD 10 may compare the heart rate of patient 4 with one or more arrhythmia thresholds to determine whether to trigger detection of an arrhythmia episode. In some examples, to compare the heart rate of patient 4 with an arrhythmia threshold, external device 12 and/or IMD 10 may compare one or more measured cardiac cycle lengths of patient 4 to a cardiac cycle length threshold, and may trigger detection of the arrhythmia episode if the cardiac cycles of patient 4 during the measured cardiac cycle length meets a number of intervals to detect associated with the cardiac cycle length threshold, such as by meeting the arrhythmia threshold for x out of y cardiac cycles during the measured cardiac cycle length, or by meeting the arrhythmia threshold for n consecutive cardiac cycles during the cardiac cycle length or estimate an average/median heart rate estimated over a time window.

In some examples, external device 12 may compare the heart rate of patient 4 with the tachycardia threshold to determine whether to trigger detection of a tachyarrhythmia episode for patient 4. More specifically, if external device 12 determines that the heart rate of patient 4 is higher than or equal to the tachycardia threshold, external device 12 may trigger detection of a tachyarrhythmia episode for patient 4. The tachyarrhythmia episode may last until the heart rate is lower than the tachycardia threshold. Thus, once external device 12 has triggered detection of the tachyarrhythmia episode, external device 12 may end detection of the tachyarrhythmia episode in response to determining that patient 4's heart rate is lower than the tachycardia threshold.

In some examples, external device 12 and/or IMD 10 determining whether the heart rate of patient 4 is higher than or equal to the tachycardia threshold may include determining whether the heart rate of patient 4 is greater than or equal to the tachycardia threshold over the cardiac cycle length threshold associated with the tachycardia threshold. For example, external device 12 and/or IMD 10 may determine whether the number of cardiac cycles during a measured cardiac cycle length in which the heart rate of patient 4 is higher than or equal to the tachycardia threshold meets a number of intervals to detect associated with the cardiac cycle length threshold.

In some examples, external device 12 and/or IMD 10 may compare the heart rate of patient 4 with the bradycardia threshold to determine whether to trigger detection of a bradyarrhythmia episode for patient 4. More specifically, if external device 12 and/or IMD 10 determines that the heart rate of patient 4 is lower than or equal to the tachycardia threshold, external device 12 and/or IMD 10 may trigger detection of a bradyarrhythmia episode for patient 4. The bradyarrhythmia episode may last until the heart rate is higher than the bradycardia threshold. Thus, once external device 12 and/or IMD 10 has triggered detection of the bradyarrhythmia episode, external device 12 and/or IMD 10 may end detection of the bradyarrhythmia episode in response to determining that patient 4's heart rate is higher than the bradycardia threshold. External device 12 and/or IMD 10 may compare the heart rate of patient 4 with any other suitable heart rate thresholds to determine whether to trigger any other suitable arrhythmia episodes.

In some examples, external device 12 and/or IMD 10 determining whether the heart rate of patient 4 is lower than or equal to the bradycardia threshold may include determining whether the heart rate of patient 4 is lower than or equal to the bradycardia threshold over the cardiac cycle length threshold associated with the bradycardia threshold. For example, external device 12 and/or IMD 10 may determine whether the number of cardiac cycles during a measured cardiac cycle length in which the heart rate of patient 4 is lower than or equal to the bradycardia threshold meets a number of intervals to detect associated with the cardiac cycle length threshold or estimate an average/median heart rate estimated over a time window.

External device 12 and/or IMD 10 may, in response to triggering detection of an arrhythmia episode for patient 4, capture data associated with the arrhythmia episode until the end of detection of the arrhythmia episode. The data captured by external device 12 and/or IMD 10 may include cardiac electrogram data of patient 4 during the arrhythmia episode, the heart rate of patient 4 at the onset of the arrhythmia episode and throughout the arrhythmia episode, the duration of the arrhythmia episode, and any other relevant information. In some examples, external device 12 and/or IMD 10 may, in response to triggering detection of a tachyarrhythmia episode for patient 4, collect information associated with the tachyarrhythmia episode, such as the duration of the tachyarrhythmia episode (i.e., the amount of time the heart rate of patient 4 is equal to or above the tachycardia threshold), the cardiac electrogram data of patient 4 during the tachyarrhythmia episode, the granular heart rate values of patient 4 during the tachyarrhythmia episode, the heart rate value of patient 4 at the onset of the tachyarrhythmia episode, and the like.

In some examples, external device 12 and/or IMD 10 may, in response to triggering detection of a bradyarrhythmia episode for patient 4, collect information associated with the bradyarrhythmia episode, such as the duration of the bradyarrhythmia episode (i.e., the amount of time the heart rate of patient 4 is equal to or below the bradycardia threshold), the cardiac electrogram data of patient 4 during the bradyarrhythmia episode, the granular heart rate values of patient 4 during the bradyarrhythmia episode, the heart rate value of patient 4 at the onset of the bradyarrhythmia episode, and the like. In some examples, external device 12 and/or IMD 10 may perform filtering of the heart rate values of patient 4 for noise that may be introduced due to the elevated activity level of patient 4. For example, external device 12 and/or IMD 10 may compare the morphology of the depolarizations detected in the signal to one or more templates to filter out depolarizations that are not consistent with the arrhythmia and may accordingly recalculate the cycle lengths and heart rates captured by external device 12 and/or IMD 10. As such, external device 12 and/or IMD 10 may apply an artificial filter such as a QRS morphology similarity measure to the heart rate values of patient 4 to help ensure that non-artifact episodes are captured.

In some example, in response to triggering detection of a bradyarrhythmia episode for patient 4, external device 12 may output an alert, such as an audible alert, visible alert, haptic alert, and the like, to alert patient 4 that detection of the bradyarrhythmia episode has been triggered. Patient 4 may, in response, cause external device 12 to start collecting information (e.g., ECGs) associated with the bradyarrhythmia episode by interacting with external device 12. For example, external device 12 may, in response to triggering detection of a bradyarrhythmia episode for patient 4, receive one or more user input from patient 4, such as by patient 4 pressing a button on external device 12 or otherwise touching external device 12, that indicates a request by patient 4 to start collecting information associated with the bradyarrhythmia episode. External device 12 may, in response to receiving user input indicative of a request by patient 4 to start collecting information associated with the bradyarrhythmia episode, collect information associated with the bradyarrhythmia episode, as described above.

External device 12 and/or IMD 10 may send the information associated with the arrhythmia episode to a monitoring center, such as via a wireless network connection and/or over the Internet, so that the monitoring center may analyze the information associated with the arrhythmia episode to create an arrhythmia report for review by, for example, a clinician. In the case of certain notifiable events, the monitoring center may be able to proactively and urgently notify patient 4's physician of the notifiable events. In some examples, the monitoring center may analyze information associated with a tachyarrhythmia episode to determine trends such as heart rate variability during the tachyarrhythmia episode and the acceleration and/or deceleration of the heart rate during the tachyarrhythmia episode. In some examples, the monitoring center may analyze information associated with a bradyarrhythmia episode to derive a heart rate to activity level correlation for patient 4 and the heart rate response of patient 4 to levels of activity.

The techniques of the disclosure may provide specific improvements to the field of cardiac arrhythmia detection by medical devices such as external device 12 and IMD 10. For example, the techniques of the disclosure may enable medical devices such as external device 12 to capture diagnostically relevant arrhythmia episodes that may not be captured by medical devices that do not adjust heart rate threshold levels based on the activity levels of the patient, thereby improving the functioning of cardiac arrhythmia detection and monitoring devices.

Figure 2:
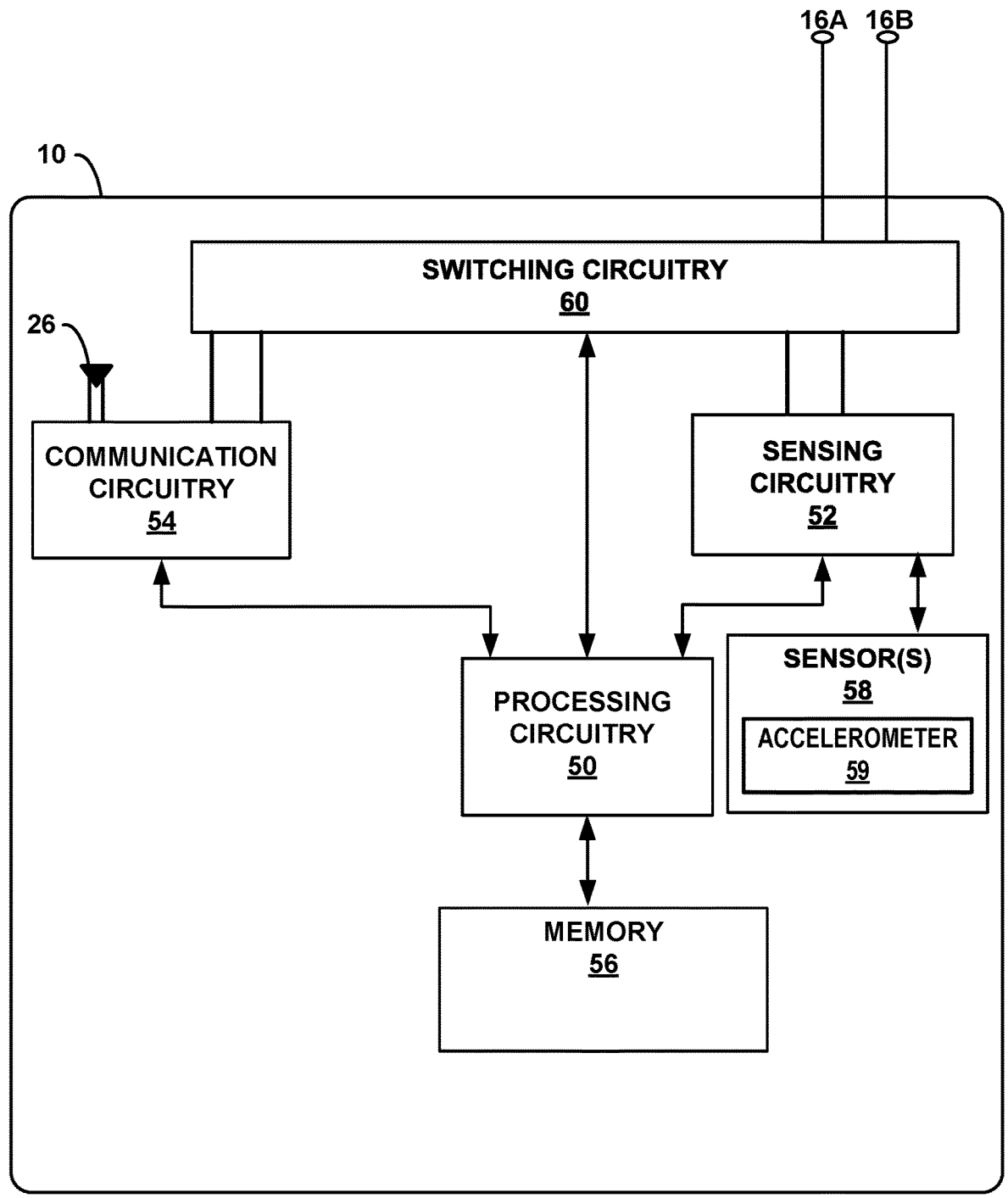
FIG. 2 is a block diagram illustrating an example of the implantable medical device of FIG. 1.

FIG. 2 is a block diagram illustrating an example of the implantable medical device of FIG. 1. As shown in FIG. 2, IMD 10 includes processing circuitry 50 sensing circuitry 52, communication circuitry 54, memory 56, sensors 58, switching circuitry 60, and electrodes 16A, 16B (hereinafter "electrodes 16"), one or more of which may be disposed within a housing of IMD 10. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 and communication circuitry 54 may be selectively coupled to electrodes 16A, 16B via switching circuitry 60 as controlled by processing circuitry 50. Sensing circuitry 52 may monitor signals from electrodes 16A, 16B in order to monitor electrical activity of a heart of patient 4 of FIG. 1 and produce heart-related data for patient 4, such as the heart rate, cardiac electrogram data, and the like for patient 4. In some examples, processing circuitry 50 transmits, via communication circuitry 54, the cardiac electrogram data for patient 4 to an external device, such as external device 12 of FIG. 1. For example, IMD 10 sends digitized cardiac electrogram data to external device 12 of FIG. 1. In some examples, IMD 10 transmits one or more segments of the cardiac electrogram data in response to instructions from external device 12 (e.g., when external device 12 requests triggered arrhythmia episodes).

In some examples, IMD 10 includes one or more sensors 58, such as one or more accelerometers 59, temperature sensors, microphones, and/or pressure sensors. Sensing circuitry 52 may monitor signals from sensors 58, and processing circuitry 50 may analyze patient data obtained from sensors 58, and/or transmit the patient data to an external device, such as external device 12 of FIG. 1, for analysis. In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter.

One or more sensors 58 may also include motion sensing circuitry that is operable to sense the motion of IMD 10 and, by being implanted in patient 4, to sense the motion of patient 4. Such motion sensing circuitry may include one or more of: accelerometers, gyroscopes, and/or other motion sensors that may be able to sense one or more types of motion such as linear acceleration, rotation, steps, and the like and to output values indicative of the motion sensed by the one or more sensors. For example, IMD 10 may include accelerometer 59 that is operable to measure acceleration forces along multiple axis and to output accelerometer data, which may be values of the acceleration forces measured by accelerometer 59, such as a three-axis accelerometer that measures acceleration forces along x, y, and z axis, and accelerometer 59 may output the values of the acceleration forces measured by the accelerometer along each of the axis. One or more sensors 58, such as accelerometer 59, may continually measure the motion of IMD 10 and patient 4, and may continually output sensor values associated with the measured motion of IMD 10 and patient 4.

Communication circuitry 54 may include any suitable hardware, firmware, software or any combination thereof for communicating with another device, such as external device 12 or another medical device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., communication circuitry 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select one or more parameters defining how IMD 10 senses cardiac electrogram data of patient 4.

One or more components of IMD 10 may be coupled a power source (not depicted in FIG. 2), which may include a rechargeable or non-rechargeable battery positioned within a housing of IMD 10. A non-rechargeable battery may be selected to last for several years, while a rechargeable battery may be inductively charged from an external device, e.g., on a daily or weekly basis.

In some examples, processing circuitry 50 may be configured to monitor patient 4 to detect arrhythmia episodes. More specifically, processing circuitry 50 may be configured to monitor the activity level of patient 4 and to determine one or more heart rate thresholds for triggering detection of arrhythmia episodes based at least in part on the activity level of patient 4.

Processing circuitry 50 may be configured to enable IMD 10 to operate in one or more of a plurality of monitoring modes for cardiac monitoring of patient 4. In some examples, the plurality of monitoring modes may include a heart failure monitoring mode, a mobile cardiac telemetry/Holter-type arrhythmia monitoring mode, a functional chronotropic incompetence monitoring mode, and the like. IMD 10 may operate in two or more of the plurality of monitoring modes at the same time. For example, because atrial fibrillation is a co-morbidity with heart failure, IMD 10 may operate in both heart failure monitoring mode and mobile cardiac telemetry/Holter-type arrhythmia monitoring mode. Thus, in some examples, IMD 10 may operate in both heart failure monitoring mode and mobile cardiac telemetry/Holter-type arrhythmia monitoring mode, in both mobile cardiac telemetry/Holter-type arrhythmia monitoring mode and functional chronotropic incompetence monitoring mode, in both heart failure monitoring mode and functional chronotropic incompetence monitoring mode, and the like.

When IMD 10 operates in a heart failure monitoring mode, processing circuitry 50 may be configured to determine whether to trigger detection of a tachyarrhythmia episode by determining whether the heart rate of patient 4 is greater than or equal to a tachycardia threshold. When IMD 10 operates in a heart failure monitoring mode, processing circuitry 50 may be configured to determine whether to trigger detection of a tachyarrhythmia episode based at least in part on determining whether the heart rate of patient 4 is greater than or equal to a tachycardia threshold. When IMD 10 operates in a functional chronotropic incompetence monitoring mode, processing circuitry 50 may be configured to determine whether to trigger detection of a bradyarrhythmia episode based at least in part on determining whether the heart rate of patient 4 is less than or equal to a bradycardia threshold. When IMD 10 operates in a mobile cardiac telemetry/Holter-type arrhythmia monitoring mode, processing circuitry 50 may be configured to determine whether to trigger detection a bradyarrhythmia episode based at least in part on determining whether the heart rate of patient 4 is less than or equal to a bradycardia threshold, and to determine whether to trigger detection of a tachyarrhythmia episode based at least in part on determining whether the heart rate of patient 4 is greater than or equal to a tachycardia threshold.

Processing circuitry 50 may be configured to adjust one or more heart rate thresholds for triggering detection of an arrhythmia episode for patient 4 based at least in part on the activity level of patient 4. The activity level of patient 4 may correspond to patient 4's activity intensity at the moment, and processing circuitry 50 may be configured to categorize the activity intensity of patient 4 into one of a plurality of activity levels of patient 4. The plurality of activity levels, in order of increasing activity, may include patient 4 being at rest, patient 4 being mildly active, patient 4 being moderately active, and patient 4 being highly active. Processing circuitry 50 may also determine any other appropriate activity levels of patient 4.

Processing circuitry 50 may be configured to determine the activity intensity of patient 4 based at least in part on sensor values received from one or more sensors 58, such as from accelerometer 59, that correspond to the motion of IMD 10. Processing circuitry 50 may be configured to continually receive, from one or more sensors 3258 sensor values that correspond to the motion of IMD 10 and may be configured to determine, based at least in part on the sensor values, the activity intensity of patient 4. Because IMD 10 is implanted in patient 4, the motion sensed by one or more sensors 58 may correspond to the motion of patient 4, and the sensor values generated by one or more sensors 58 that correspond to the motion sensed by the one or more sensors may be indicative of the activity intensity of patient 4. Processing circuitry 50 may therefore be configured to determine the activity level of patient 4 based at least in part on the sensor values generated by one or more sensors 58 using any suitable technique or algorithm.

In some examples, processing circuitry 50 may be configured to determine the activity level of patient 4 based at least in part on the magnitude of the sensor values received from one or more sensors 58. For example, processing circuitry 50 may be configured to determine the average magnitude of the sensor values over a specified time period (e.g., 1 second, 30 seconds, 1 minute, etc.) and may compare the average magnitude to one or more threshold values that correspond to different activity levels. For example, a first threshold value may correspond to low activity level, a second threshold value higher than the first threshold value may correspond to a moderate activity level, and a third threshold value higher than the second threshold value may correspond to a high activity level. Thus, for example, if the average magnitude of the sensor values is lower than the first threshold value, then processing circuitry 50 may be configured to determine that patient 4 is at rest. In another example, if the average magnitude is higher than the second threshold value but lower than the third threshold value, then processing circuitry 50 may be configured to determine that the activity level of patient 4 is moderate. Processing circuitry 50 may also be configured to perform any other suitable technique to determine the activity level of patient 4 based at least in part on the sensor values generated by one or more sensors 58.

Processing circuitry 50 may be configured to determine one or more thresholds for triggering detection of an arrhythmia episode based at least in part on the activity level of patient 4 indicated by the one or more sensor values. In some examples, processing circuitry 50 may be configured to determine the tachycardia threshold for patient 4 based at least in part on the activity level of patient 4. Processing circuitry 50 may be configured to determine whether the activity level of patient 4 determined from the sensor values indicate that patient 4 is at rest, and may determine whether patient 4 has been at rest for at least a minimum resting duration (e.g., one minute, two minutes, and the like). If processing circuitry 50 determines that patient 4 has been at rest for at least the specified amount of time, processing circuitry 50 may be configured to set the tachycardia threshold for patient 4 to a specified heart rate. For example, because a resting heart rate of above 80 BPM in heart failure patients may be an indicator of worsening of heart failure, processing circuitry 50 may be configured to lower the tachycardia threshold for patient 4 from 120 BPM to 80 BPM in response to determining that patient 4 has been at rest for at least a minimum resting duration.

In some examples, processing circuitry 50 may be configured to determine the bradycardia threshold for patient 4 based at least in part on the activity level of patient 4. Processing circuitry 50 may be configured to determine whether the activity level of patient 4 determined from the sensor values indicate that patient 4 is at least moderately active and may, upon determining that patient 4 is at least moderately active, adjust the bradycardia threshold for patient 4. For example, if processing circuitry 50 determines that patient 4 is moderately active but not highly active, processing circuitry 50 may be configured to set the bradycardia threshold for patient 4 to a threshold associated with a moderate activity level of patient 4. In some examples, processing circuitry 50 may determine the threshold associated with a moderate activity of patient 4 as 0.4 times the age-predicted maximal heart rate (APMHR) for patient 4. If processing circuitry 50 determines that patient 4 is highly active, processing circuitry 50 may be configured to set the bradycardia threshold for patient 4 to a threshold associated with a high activity level of patient 4. In some examples, processing circuitry 50 may determine the threshold associated with a high activity of patient 4 as 0.6 times the age-predicted maximal heart rate (APMHR) for patient 4.

Processing circuitry 50 may be configured to continually receive sensor values from one or more sensors 32 indicative of the motion of patient 4 and may continually determine the activity level of patient 4 based on the received sensor values. Processing circuitry 50 may therefore also be configured to continually determine heart rate thresholds based on updates to the activity level of patient 4 determined by processing circuitry 50. For example, if processing circuitry 50 determines, after adjusting the tachycardia threshold to 80 BPM based on patient 4 being at rest, that patient 4 is no longer at rest, processing circuitry 50 may be configured to re-raise the tachycardia threshold from 80 BPM to 120 BPM.

As described above, IMD 10 may operate in one or more of a plurality of operating modes, such as a heart failure monitoring mode, a mobile cardiac telemetry/Holter-type arrhythmia monitoring mode, a functional chronotropic incompetence monitoring mode, and the like. Thus, in some examples, processing circuitry 50 may be configured to determine, based on the one or more monitoring modes of IMD 10, whether to determine one or more heart rate thresholds for patient 4, so that processing circuitry 50 may be configured to determine different heart rate thresholds based on the different monitoring modes under which the IMD 10 may operate.

In some example, processing circuitry 50 may be configured to determine the tachycardia threshold for patient 4 based at least in part on the activity level of patient 4 when IMD 10 operates in heart failure monitoring mode. Thus, for example, if IMD 10 is operating in a mobile cardiac telemetry/Holter-type arrhythmia monitoring mode or a functional chronotropic incompetence monitoring mode, but is not also operating in a heart failure monitoring mode, processing circuitry 50 may not adjust the tachycardia threshold for patient 4 based at least in part on the activity level of patient 4.

In some example, processing circuitry 50 may be configured to determine the bradycardia threshold for patient 4 based at least in part on the activity level of patient 4 when IMD 10 operates in a functional chronotropic incompetence monitoring mode. Thus, for example, if IMD 10 is operating in a mobile cardiac telemetry/Holter-type arrhythmia monitoring mode or a heart failure monitoring mode, but is not also operating in a functional chronotropic incompetence monitoring mode, processing circuitry 50 may not determine the bradycardia threshold for patient 4 based at least in part on the activity level of patient 4 but may instead use preset thresholds.

Processing circuitry 50 may be configured to continually monitor the heart rate of patient 4 and to determine whether to trigger detection of one or more arrhythmia episodes based at least in part on comparing the heart rate of patient 4 with one or more heart rate thresholds. Processing circuitry 50 may continually receive indications of the heart rate of patient 4 from IMD 10 and/or one or more sensors 32 and may continually compare the heart rate of patient 4 with one or more heart rate thresholds to determine whether to trigger detection of an arrhythmia episode for patient 4.

In some examples, processing circuitry 50 may be configured to trigger detection of a tachyarrhythmia episode in response to determining that the heart rate of patient 4 is greater than or equal to the tachycardia threshold. The detection of the tachyarrhythmia episode may last until processing circuitry 50 determines that the heart rate of patient 4 is less than the tachyarrhythmia episode. Thus, once processing circuitry 50 has triggered detection of the tachyarrhythmia episode, processing circuitry 50 may be configured to end detection of the tachyarrhythmia episode in response to determining that patient 4's heart rate is lower than the tachycardia threshold.

In some examples, processing circuitry 50 may be configured to trigger detection of a bradyarrhythmia episode in response to determining that the heart rate of patient 4 is less than or equal to the bradycardia threshold. The detection of the bradyarrhythmia episode may last until processing circuitry 50 determines that the heart rate of patient 4 is greater than the bradyarrhythmia episode. Thus, once processing circuitry 50 has triggered detection of the bradyarrhythmia episode, processing circuitry 50 may be configured to end detection of the bradyarrhythmia episode in response to determining that patient 4's heart rate is higher than the bradycardia threshold.

Processing circuitry 50 may be configured to, in response to triggering detection of an arrhythmia episode for patient 4, capture data associated with the arrhythmia episode until the end of the detection of the arrhythmia episode. The data captured by processing circuitry 50 may include heart rate of patient 4 at the onset of the arrhythmia episode and throughout the arrhythmia episode, the duration of the arrhythmia episode, and any other relevant information. In some examples, processing circuitry 50 may be configured to, in response to triggering detection of a tachyarrhythmia episode for patient 4, collect information associated with the tachyarrhythmia episode, such as the duration of the tachyarrhythmia episode (i.e., the amount of time the heart rate of patient 4 is equal to or above the tachycardia threshold), the granular heart rate values of patient 4 during the tachyarrhythmia episode, the heart rate value of patient 4 at the onset of the tachyarrhythmia episode, and the like.

In some examples, processing circuitry 50 may be configured to, in response to triggering detection of a bradyarrhythmia episode for patient 4, collect information associated with the bradyarrhythmia episode, such as the duration of the bradyarrhythmia episode (i.e., the amount of time the heart rate of patient 4 is equal to or below the bradycardia threshold), the granular heart rate values of patient 4 during the bradyarrhythmia episode, the heart rate value of patient 4 at the onset of the bradyarrhythmia episode, and the like. In some examples, processing circuitry 50 may be configured to filter of the heart rate values of patient 4 for noise that may be introduced due to the elevated activity level of patient 4. As such, processing circuitry 50 may be configured to apply an artificial filter such as a QRS morphology similarity measure to the heart rate values of patient 4 to help ensure that non-artifact episodes are captured.

Processing circuitry 50 may be configured to send the information associated with detection of the arrhythmia episode to a monitoring center, such as on a remote computing system, so that the monitoring center may analyze the information associated with the arrhythmia episode to create an arrhythmia report for review by, for example, a clinician. In the case of certain notifiable events, the monitoring center may be able to proactively and urgently notify patient 4's physician of the notifiable events. In some examples, the monitoring center may analyze information associated with detection of a tachyarrhythmia episode to determine trends such as heart rate variability during the tachyarrhythmia episode and the acceleration and/or deceleration of the heart rate during the tachyarrhythmia episode. In some examples, the monitoring center may analyze information associated with detection of a bradyarrhythmia episode to derive a heart rate to activity level correlation for patient 4 and the heart rate response of patient 4 to levels of activity.

Figure 3:
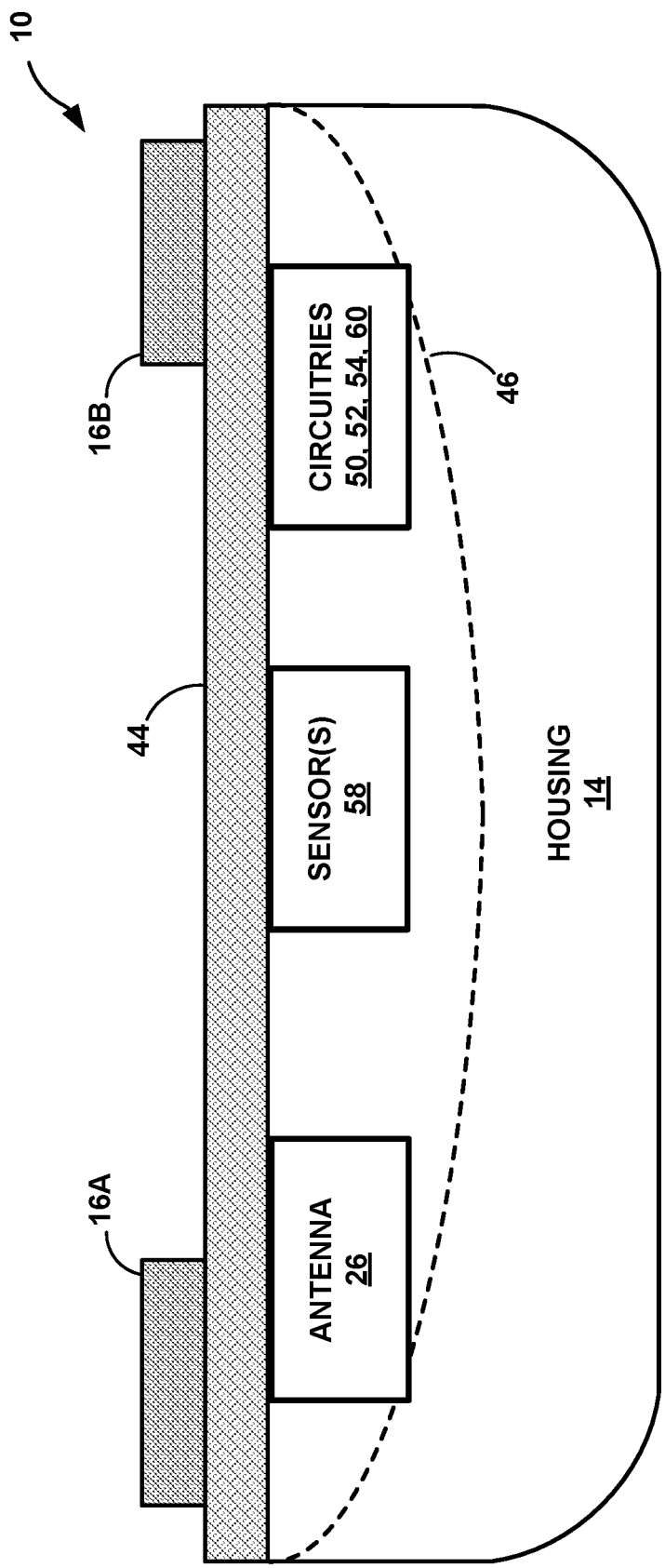
FIG. 3 is a block diagram illustrating an example configuration of the implantable medical device of FIG. 1.

FIG. 3 is a block diagram illustrating an example configuration of implantable medical device of FIG. 1. The components of FIG. 3 may not necessarily be drawn to scale, but instead may be enlarged to show detail. Specifically, FIG. 3 is a block diagram of a top view of an example configuration of an IMD 10 of FIG. 1.

FIG. 3 is a conceptual drawing illustrating an example IMD 10 that may include components substantially similar to IMD 10 of FIG. 1. In addition to the components illustrated in FIGS. 1 and 2, the example of IMD 10 illustrated in FIG. 3 also may include a wafer-scale insulative cover 44, which may help insulate electrical signals passing between electrodes 16A, 16B on housing 14 and processing circuitry 50. In some examples, insulative cover 44 may be positioned over an open housing 14 to form the housing for the components of IMD 10B. One or more components of IMD 10B (e.g., communication circuitry 26, processing circuitry 50, sensing circuitry 52, communication circuitry 54, and/or switching circuitry 60) may be formed on a bottom side of insulative cover 44, such as by using flip-chip technology. Insulative cover 44 may be flipped onto housing 14. When flipped and placed onto housing 14, the components of IMD 10 formed on the bottom side of insulative cover 44 may be positioned in a gap 46 defined by housing 14. Housing 14 may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

In some examples, IMD 10 collects, via sensing circuitry 50 and/or sensors 58, patient data of patient 4 including cardiac electrogram data. Sensors 58 may include one or more sensors, such as one or more accelerometers, pressure sensors, optical sensors for 02 saturation, etc. In some examples, the patient data includes one or more of an activity level of the patient, a heartrate of the patient, a posture of the patient, a cardiac electrogram of the patient, a blood pressure of the patient, accelerometer data for the patient, or other types of patient parametric data. In some examples, IMD 10 uploads, via communication circuitry 54, the patient data to external device 12, which may in turn upload such data to a remote monitoring center or patient monitoring network.

Figure 4:
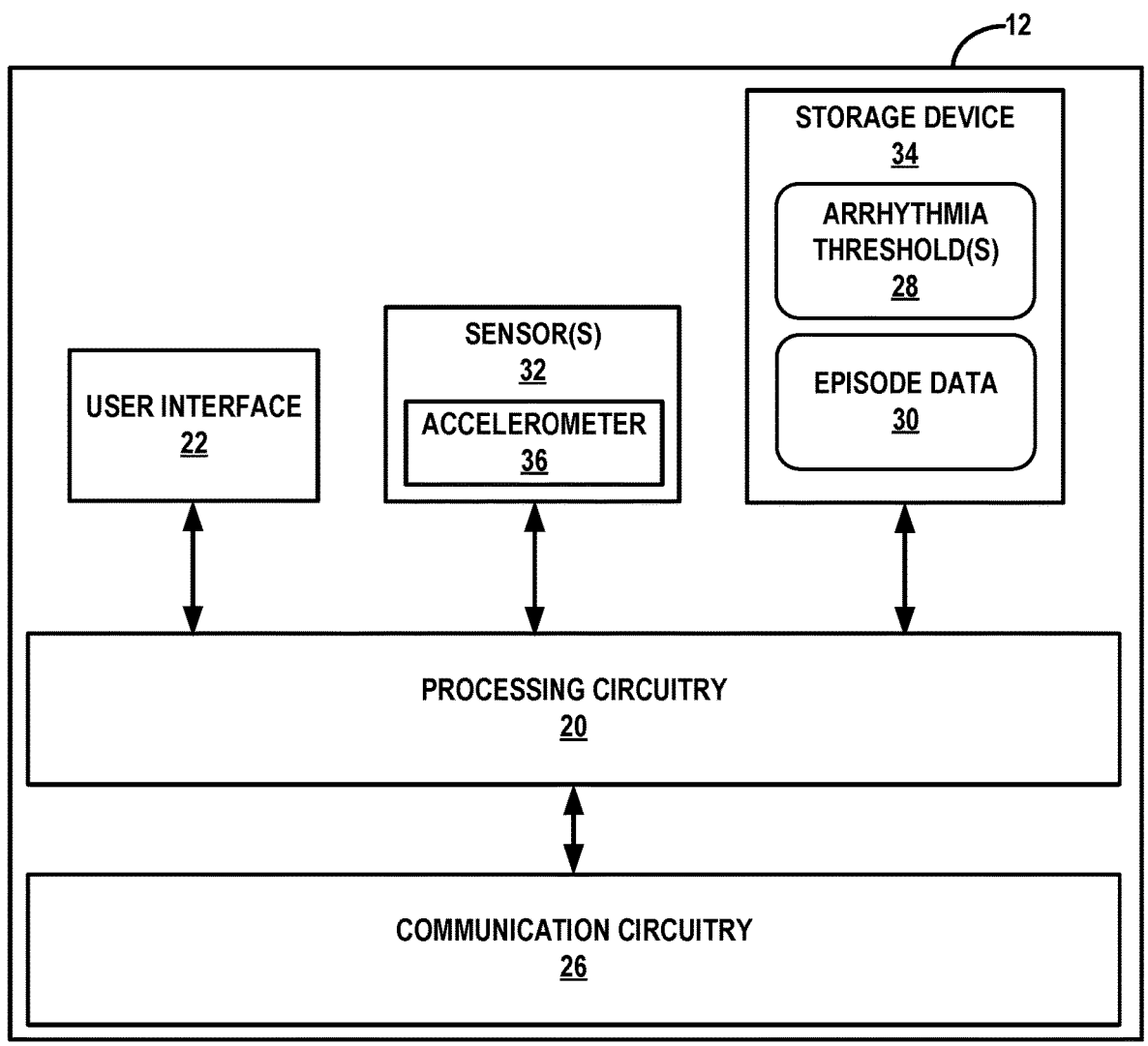
FIG. 4 is a block diagram illustrating an example configuration of the external device of FIG. 1.

FIG. 4 is a block diagram illustrating an example configuration of external device 12 of FIG. 1. In the example of FIG. 4, the at least one external device 12 includes processing circuitry 20, communication circuitry 26, one or more sensors 32, storage device 34, and user interface device 22.

Processing circuitry 20 may include one or more processors that are configured to implement functionality and/or process instructions for execution within external device 12. For example, processing circuitry 20 may be capable of processing instructions stored in storage device 34. Processing circuitry 20 may include, for example, microprocessors, a digital signal processors (DSPs), an application specific integrated circuits (ASICs), field-programmable gate arrays (FPGAs), complex programmable logic devices (CPLDs), or equivalent integrated or discrete logic circuitry, or a combination of any of the foregoing devices or circuitry. Accordingly, processing circuitry 20 may include any suitable structure, whether in hardware, software, firmware, or any combination thereof, to perform the functions ascribed herein to processing circuitry 20.

User interface device 22 includes a display (not shown), such as a liquid crystal display (LCD) or a light emitting diode (LED) display or other type of screen, with which processing circuitry 20 may present health- or device-related information, e.g., cardiac EGMs, indications of detections of impedance changes, temperature changes, etc. In addition, user interface device 22 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interface device 22 presented by processing circuitry 20 of external device 12 and provide input.

Communication circuitry 26 may include any suitable hardware, firmware, software or any combination thereof for communicating with another device, such as IMD 10. Under the control of processing circuitry 20, communication circuitry 26 may receive downlink telemetry from, as well as send uplink telemetry to, IMD 10, or another device. Communication circuitry 26 may be configured to transmit or receive signals via inductive coupling, electromagnetic coupling, NFC, RF communication, Bluetooth®, Wi-Fi™, or other proprietary or non-proprietary wireless communication schemes. Communication circuitry 26 may also be configured to communicate with devices other than IMD 10 via any of a variety of forms of wired and/or wireless communication and/or network protocols.

Data exchanged between external device 12, computing system 24 and IMD 10 may include operational parameters of IMD 10. External device 12 may transmit data, including computer-readable instructions, to IMD 10. IMD 10 may receive and implement the computer-readable instructions. In some examples, the computer-readable instructions, when implemented by IMD 10, may control IMD 10 to change one or more operational parameters, export collected data, etc. In some examples, external device 12 may be coupled to external electrodes, or to implanted electrodes via percutaneous leads. In such examples, external device 12 may receive, from IMD 10, and monitor physiological parameters, ECGs, etc., according to one or more techniques disclosed herein.

One or more sensors 32 may be configured to sense, measure, and/or collect information regarding external device 12 and/or patient 4. In some examples, one or more sensors 32 may include heart monitoring circuitry that is operable to monitor electrical activity of a heart of patient 4 of FIG. 1 and produce cardiac electrogram data for patient 4. In this case, external device 12 may be able to determine the heart rate of patient 4 and to produce cardiac electrogram data for patient 4 without receiving such data from IMD 10.

One or more sensors 32 may also include motion sensing circuitry that is operable to sense the motion of external device 12 and, by being worn by patient 4, to sense the motion of patient 4. Such motion sensing circuitry may include one or more of: accelerometers, gyroscopes, and/or other motion sensors that may be able to sense one or more types of motion such as linear acceleration, rotation, steps, and the like and to output values indicative of the motion sensed by the one or more sensors. For example, external device 12 may include accelerometer 36 that is operable to measure acceleration forces along multiple axis and to output accelerometer data, which may be values of the acceleration forces measured by accelerometer 36, such as a three-axis accelerometer that measures acceleration forces along x, y, and z axis, and accelerometer 36 may output the values of the acceleration forces measured by the accelerometer along each of the axis. One or more sensors 32, such as accelerometer 36, may continually measure the motion of external device 12 and may continually output sensor values associated with the measured motion of external device 12.

Storage device 34 may be configured to store information within external device 12 during operation. Storage device 34 may include a computer-readable storage medium or computer-readable storage device. In some examples, storage device 34 includes one or more of a short-term memory or a long-term memory. Storage device 34 may include, for example, read-only memory (ROM), random access memory (RAM), non-volatile RAM (NVRAM), Dynamic RAM (DRAM), Static RAM (SRAM), magnetic discs, optical discs, flash memory, forms of electrically-erasable programmable ROM (EEPROM) or erasable programmable ROM (EPROM), or any other digital media. In some examples, storage device 34 is used to store data indicative of instructions for execution by processing circuitry 20. Storage device 34 may also be used to store data as a result of operations performed by processing circuitry 20.

Processing circuitry 20 may be configured to monitor patient 4 for arrhythmia episodes. More specifically, processing circuitry 20 may be configured to monitor the activity level of patient 4 and to determine one or more heart rate thresholds for triggering detection of arrhythmia episodes based at least in part on the activity level of patient 4.

Processing circuitry 20 may be configured to enable external device 12 to operate in one or more of a plurality of monitoring modes for cardiac monitoring of patient 4. In some examples, the plurality of monitoring modes may include a heart failure monitoring mode, a mobile cardiac telemetry/Holter-type arrhythmia monitoring mode, a functional chronotropic incompetence monitoring mode, and the like. External device 12 may operate in two or more of the plurality of monitoring modes at the same time. For example, because atrial fibrillation is a co-morbidity with heart failure, external device 12 may operate in both heart failure monitoring mode and mobile cardiac telemetry/Holter-type arrhythmia monitoring mode. Thus, in some examples, external device 12 may operate in both heart failure monitoring mode and mobile cardiac telemetry/Holter-type arrhythmia monitoring mode, in both mobile cardiac telemetry/Holter-type arrhythmia monitoring mode and functional chronotropic incompetence monitoring mode, in both heart failure monitoring mode and functional chronotropic incompetence monitoring mode, and the like.

When external device 12 operates in a heart failure monitoring mode, processing circuitry 20 may be configured to determine whether to trigger detection of a tachyarrhythmia episode based at least in part on determining whether the heart rate of patient 4 is greater than or equal to a tachycardia threshold. When external device 12 operates in a functional chronotropic incompetence monitoring mode, processing circuitry 20 may be configured to determine whether to trigger detection a bradyarrhythmia episode based at least in part on determining whether the heart rate of patient 4 is less than or equal to a bradycardia threshold. When external device 12 operates in a mobile cardiac telemetry/Holter-type arrhythmia monitoring mode, processing circuitry 20 may be configured to determine whether to trigger detection of a bradyarrhythmia episode based at least in part on determining whether the heart rate of patient 4 is less than or equal to a bradycardia threshold, and to determine whether to trigger detection of a tachyarrhythmia episode based at least in part on determining whether the heart rate of patient 4 is greater than or equal to a tachycardia threshold.

Processing circuitry 20 may be configured to determine one or more heart rate thresholds for triggering an arrhythmia episode for patient 4 based at least in part on the activity level of patient 4. The activity level of patient 4 may correspond to patient 4's activity intensity at the moment, and processing circuitry 20 may be configured to categorize the activity intensity of patient 4 into one of a plurality of activity levels of patient 4. The plurality of activity levels, in order of increasing activity, may include patient 4 being at rest, patient 4 being mildly active, patient 4 being moderately active, and patient 4 being highly active.

Processing circuitry 20 may be configured to determine the activity intensity of patient 4 based at least in part on sensor values received from one or more sensors 32 that correspond to the motion of external device 12. Processing circuitry 20 may be configured to continually receive, from one or more sensors 32, such as from accelerometer 36, sensor values that correspond to the motion of external device 12 and may be configured to determine, based at least in part on the sensor values, the activity intensity of patient 4. Because external device 12 is worn by patient 4, the motion sensed by one or more sensors 32 may correspond to the motion of patient 4, and the sensor values generated by one or more sensors 32 that correspond to the motion sensed by the one or more sensors may be indicative of the activity intensity of patient 4. Processing circuitry 20 may therefore be configured to determine the activity level of patient 4 based at least in part on the sensor values generated by one or more sensors 32 using any suitable technique or algorithm.

In some examples, processing circuitry 20 may be configured to determine the activity level of patient 4 based at least in part on the magnitude of the sensor values received from one or more sensors 32. For example, processing circuitry 20 may be configured to determine the average magnitude of the sensor values over a specified time period (e.g., 1 second, 30 seconds, 1 minute, etc.) and may compare the average magnitude to one or more threshold values that correspond to different activity levels. For example, a first threshold value may correspond to low activity level, a second threshold value higher than the first threshold value may correspond to a moderate activity level, and a third threshold value higher than the second threshold value may correspond to a high activity level. Thus, for example, if the average magnitude of the sensor values is lower than the first threshold value, then processing circuitry 20 may be configured to determine that patient 4 is at rest. In another example, if the average magnitude is higher than the second threshold value but lower than the third threshold value, then processing circuitry 20 may be configured to determine that the activity level of patient 4 is moderate. Processing circuitry 20 may also be configured to perform any other suitable technique to determine the activity level of patient 4 based at least in part on the sensor values generated by one or more sensors 32.

Processing circuitry 20 may be configured to determine one or more thresholds for triggering an arrhythmia episode based at least in part on the activity level of patient 4 indicated by the one or more sensor values. In some examples, processing circuitry 20 may be configured to determine the tachycardia threshold for patient 4 based at least in part on the activity level of patient 4. Processing circuitry 20 may be configured to determine whether the activity level of patient 4 determined from the sensor values indicate that patient 4 is at rest, and may determine whether patient 4 has been at rest for at least a minimum resting duration (e.g., one minute, two minutes, and the like). If processing circuitry 20 determines that patient 4 has been at rest for at least the specified amount of time, processing circuitry 20 may be configured to, for example, set the tachycardia threshold for patient 4 to a specified heart rate. For example, because a resting heart rate of above 80 BPM in heart failure patients may be an indicator of worsening of heart failure, processing circuitry 20 may be configured to lower the tachycardia threshold for patient 4 from 120 BPM to 80 BPM in response to determining that patient 4 has been at rest for at least a minimum resting duration.

In some examples, processing circuitry 20 may be configured to determine the bradycardia threshold for patient 4 based at least in part on the activity level of patient 4. Processing circuitry 20 may be configured to determine whether the activity level of patient 4 determined from the sensor values indicate that patient 4 is at least moderately active and may, upon determining that patient 4 is at least moderately active, determine the bradycardia threshold for patient 4. For example, if processing circuitry 20 determines that patient 4 is moderately active but not highly active, processing circuitry 20 may be configured to set the bradycardia threshold for patient 4 to a threshold associated with a moderate activity level of patient 4. In some examples, processing circuitry 20 may set the threshold associated with a moderate activity of patient 4 as 0.4 times the age-predicted maximal heart rate (APMHR) for patient 4. If processing circuitry 20 determines that patient 4 is highly active, processing circuitry 20 may be configured to set the bradycardia threshold for patient 4 to a threshold associated with a high activity level of patient 4. In some examples, processing circuitry 20 may set the threshold associated with a high activity of patient 4 as 0.6 times the age-predicted maximal heart rate (APMHR) for patient 4.

Processing circuitry 20 may be configured to continually receive sensor values from one or more sensors 32 indicative of the motion of patient 4 and may continually determine the activity level of patient 4 based on the received sensor values. Processing circuitry 20 may therefore also be configured to continually determine heart rate thresholds based on updates to the activity level of patient 4 determined by processing circuitry 20. For example, if processing circuitry 20 determines, after setting the tachycardia threshold to 80 BPM based on patient 4 being at rest, that patient 4 is no longer at rest, processing circuitry 20 may be configured to raise the tachycardia threshold from 80 BPM to 120 BPM.

As described above, external device 12 may operate in one or more of a plurality of operating modes, such as a heart failure monitoring mode, a mobile cardiac telemetry/Holter-type arrhythmia monitoring mode, a functional chronotropic incompetence monitoring mode, and the like. Thus, in some examples, processing circuitry 20 may be configured to determine, based on the one or more monitoring modes of external device 12, whether to determine one or more heart rate thresholds for patient 4, so that processing circuitry 20 may be configured to determine different heart rate thresholds based on the different monitoring modes under which the external device 12 may operate.

In some example, processing circuitry 20 may be configured to determine the tachycardia threshold for patient 4 based at least in part on the activity level of patient 4 when external device 12 operates in heart failure monitoring mode. Thus, for example, if external device 12 is operating in a mobile cardiac telemetry/Holter-type arrhythmia monitoring mode or a functional chronotropic incompetence monitoring mode, but is not also operating in a heart failure monitoring mode, processing circuitry 20 may not determine the tachycardia threshold for patient 4 based at least in part on the activity level of patient 4.

In some example, processing circuitry 20 may be configured to determine the bradycardia threshold for patient 4 based at least in part on the activity level of patient 4 when external device 12 operates in a functional chronotropic incompetence monitoring mode. Thus, for example, if external device 12 is operating in a mobile cardiac telemetry/Holter-type arrhythmia monitoring mode or a heart failure monitoring mode, but is not also operating in a functional chronotropic incompetence monitoring mode, processing circuitry 20 may not determine the bradycardia threshold for patient 4 based at least in part on the activity level of patient 4.

Processing circuitry 20 may be configured to continually monitor the heart rate of patient 4 and to determine whether to trigger detection of one or more arrhythmia episodes based at least in part on comparing the heart rate of patient 4 with one or more heart rate thresholds. Processing circuitry 20 may continually receive indications of the heart rate of patient 4 from IMD 10 and/or one or more sensors 32 and may continually compare the heart rate of patient 4 with one or more heart rate thresholds to determine whether to trigger detection of an arrhythmia episode for patient 4.

In some examples, processing circuitry 20 may be configured to trigger detection of a tachyarrhythmia episode in response to determining that the heart rate of patient 4 is greater than or equal to the tachycardia threshold. The detection of the tachyarrhythmia episode may last until processing circuitry 20 determines that the heart rate of patient 4 is less than the tachyarrhythmia episode. Thus, once processing circuitry 20 has triggered detection of the tachyarrhythmia episode, processing circuitry 20 may be configured to end detection of the tachyarrhythmia episode in response to determining that patient 4's heart rate is lower than the tachycardia threshold.

In some examples, processing circuitry 20 may be configured to trigger detection of a bradyarrhythmia episode in response to determining that the heart rate of patient 4 is less than or equal to the bradycardia threshold. The detection of the bradyarrhythmia episode may last until processing circuitry 20 determines that the heart rate of patient 4 is greater than the bradyarrhythmia episode. Thus, once processing circuitry 20 has triggered detection of the bradyarrhythmia episode, processing circuitry 20 may be configured to end detection of the bradyarrhythmia episode in response to determining that patient 4's heart rate is higher than the bradycardia threshold.

Processing circuitry 20 may be configured to, in response to triggering detection of an arrhythmia episode for patient 4, capture data associated with the arrhythmia episode until the end of detection of the arrhythmia episode. The data captured by processing circuitry 20 may include heart rate of patient 4 at the onset of the arrhythmia episode and throughout the arrhythmia episode, the duration of the arrhythmia episode, and any other relevant information. In some examples, processing circuitry 20 may be configured to, in response to triggering detection of a tachyarrhythmia episode for patient 4, collect information associated with detection of the tachyarrhythmia episode, such as the duration of the tachyarrhythmia episode (i.e., the amount of time the heart rate of patient 4 is equal to or above the tachycardia threshold), the granular heart rate values of patient 4 during the detection of the tachyarrhythmia episode, the heart rate value of patient 4 at the onset of detection of the tachyarrhythmia episode, and the like.

In some examples, processing circuitry 20 may be configured to, in response to triggering detection of a bradyarrhythmia episode for patient 4, collect information associated with the bradyarrhythmia episode, such as the duration of detection of the bradyarrhythmia episode (i.e., the amount of time the heart rate of patient 4 is equal to or below the bradycardia threshold), the granular heart rate values of patient 4 during detection of the bradyarrhythmia episode, the heart rate value of patient 4 at the onset of detection of the bradyarrhythmia episode, and the like. In some examples, processing circuitry 20 may be configured to filter of the heart rate values of patient 4 for noise that may be introduced due to the elevated activity level of patient 4. As such, processing circuitry 20 may be configured to apply an artificial filter such as a QRS morphology similarity measure to the heart rate values of patient 4 to help ensure that non-artifact episodes are captured.

Processing circuitry 20 may be configured to send the information associated with detection of the arrhythmia episode to a monitoring center, such as on a remote computing system, so that the monitoring center may analyze the information associated with detection of the arrhythmia episode to create an arrhythmia report for review by, for example, a clinician. In the case of certain notifiable events, the monitoring center may be able to proactively and urgently notify patient 4's physician of the notifiable events. In some examples, the monitoring center may analyze information associated with detection of a tachyarrhythmia episode to determine trends such as heart rate variability during detection of the tachyarrhythmia episode and the acceleration and/or deceleration of the heart rate during detection of the tachyarrhythmia episode. In some examples, the monitoring center may analyze information associated with detection of a bradyarrhythmia episode to derive a heart rate to activity level correlation for patient 4 and the heart rate response of patient 4 to levels of activity.

Figure 5A:
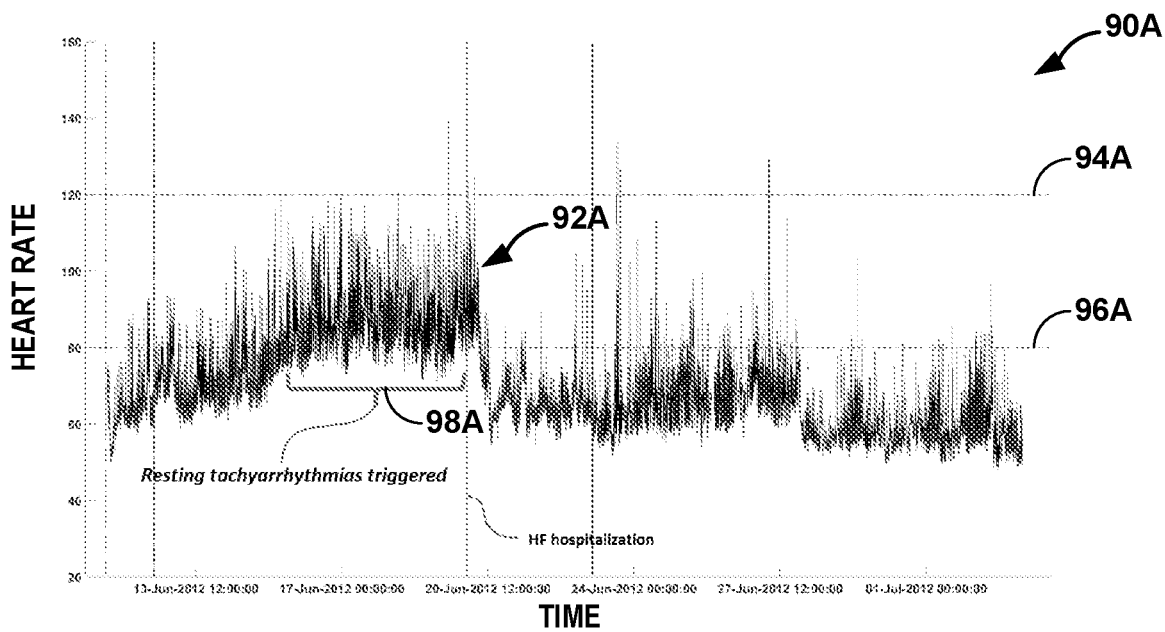
FIGS. 5A and 5B illustrate example heart rates of patients over time.
Figure 5B:
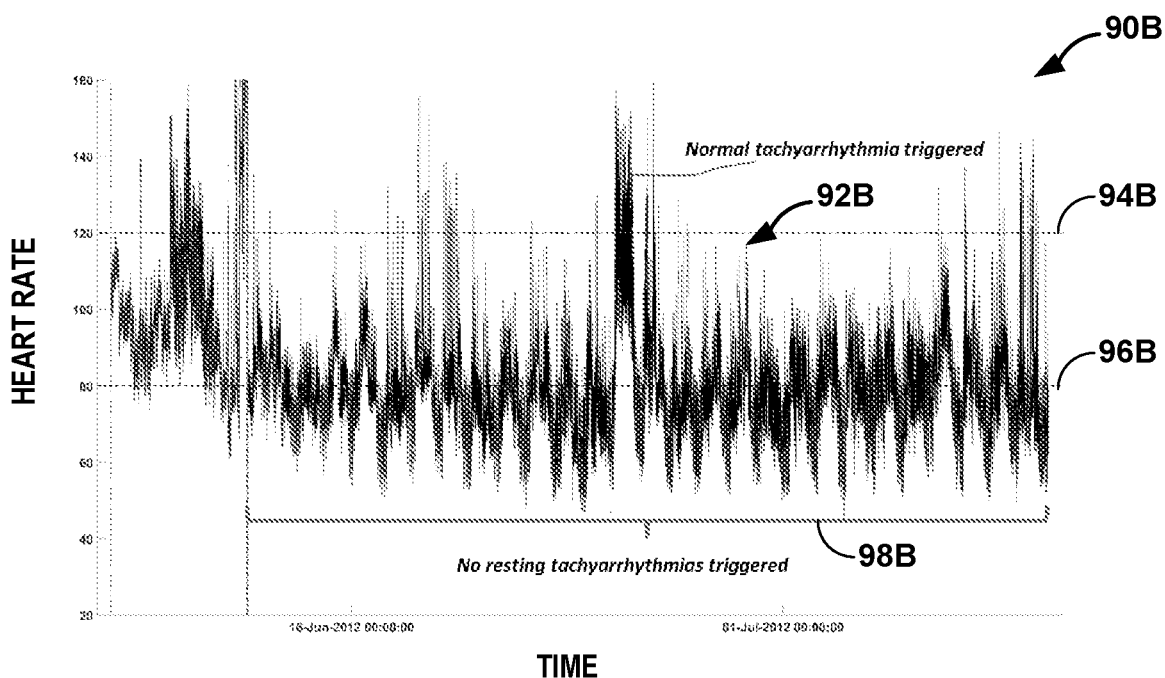

FIGS. 5A and 5B illustrate example heart rates of patients over time. As shown in FIG. 5A, graph 90A illustrates the heart rate 92A of an exemplary patient over time. When the patient is not in a resting state, the heart rate of the patient may trigger a tachyarrhythmia episode if the heart rate is above default tachycardia threshold 94A of 120 BPM. On the other hand, when the patient is in a resting state, the heart rate of the patient may trigger a tachyarrhythmia episode if the heart rate is above resting tachycardia threshold 96A of 80 BPM.

In the example of FIG. 5A, if the default tachycardia threshold 94A of 120 BPM is used for triggering a tachyarrhythmia episode, no tachyarrhythmia episodes would have been triggered for the patient because the heart rate 92A of the patient never exceeds 120 BPM for a minimum resting duration. However, when the patient is at rest, such as when the activity level of the patient is below that of resting threshold, the activity-based tachycardia threshold is lowered to resting tachycardia threshold 96A of 80 BPM. As can be seen, when the patient is at rest during time period 98A, several tachyarrhythmia episodes are triggered because the heart rate 92A of the patient exceeds resting tachycardia threshold 96A. Such tachyarrhythmia episodes may cause the physician for the patient to be informed for urgent action.

As shown in FIG. 5B, graph 90B illustrates the heart rate 92B of another exemplary patient over time. Similar to FIG. 6A, when the patient is not in a resting state, the heart rate of the patient may trigger a tachyarrhythmia episode if the heart rate is above default tachycardia threshold 94B of 120 BPM. On the other hand, when the patient is in a resting state, the heart rate of the patient may trigger a tachyarrhythmia episode if the heart rate is above resting tachycardia threshold 96B of 80 BPM. When the patient is not in a rest state during time period 98B, the tachycardia threshold for the patient may be default tachycardia threshold 94B. Thus, during time period 98B, tachyarrhythmia episodes are not triggered for the patient when the heart rate 92B of the patient is above resting tachycardia threshold 96B. Instead, during time period 98B, tachyarrhythmia episodes may be triggered for the patient only when the heart rate 92B of the patient is above default tachycardia threshold 94B.

Figure 6:
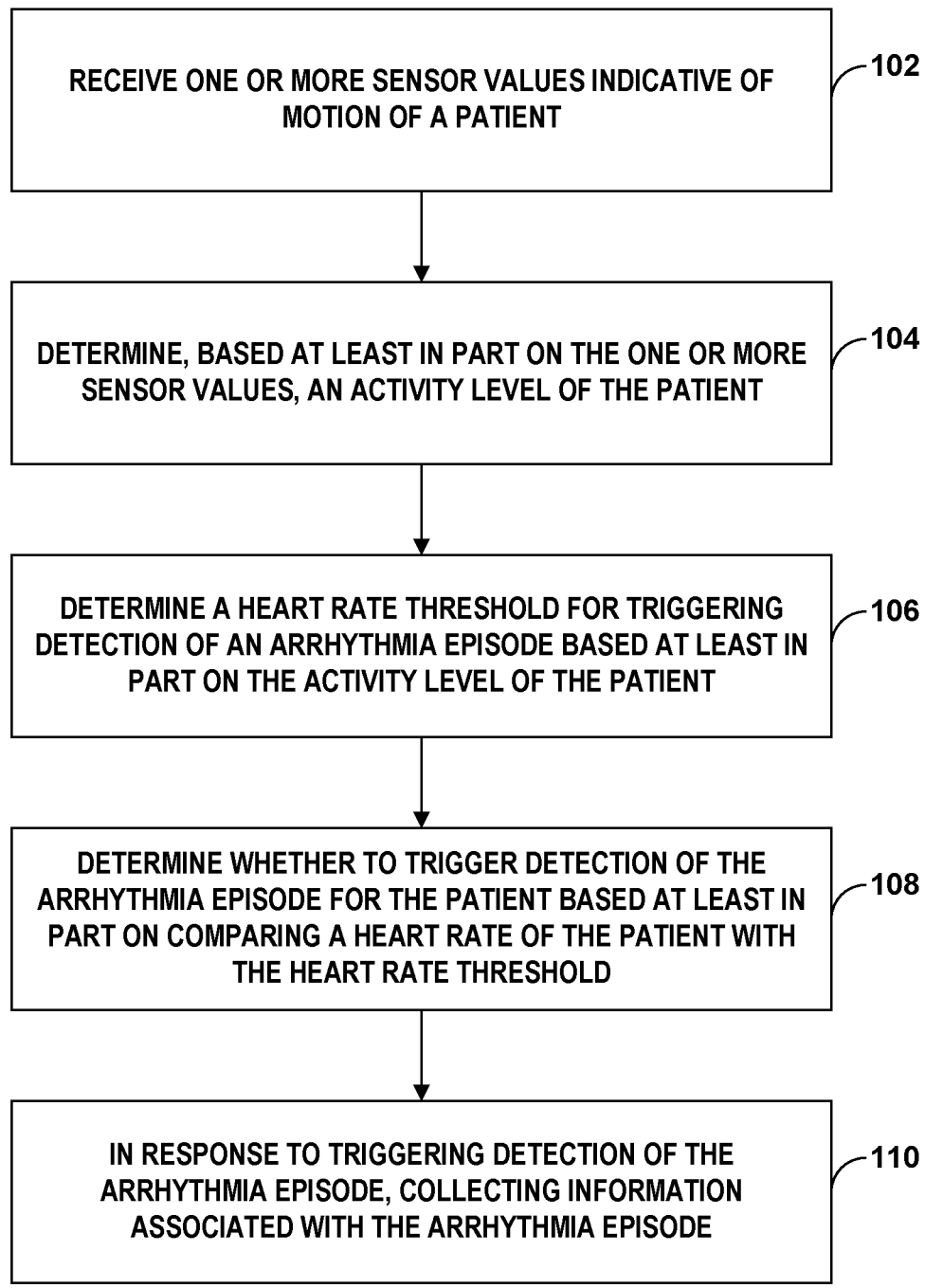
FIG. 6 is a flowchart illustrating an example operation in accordance with the techniques of the disclosure.

FIG. 6 is a flowchart illustrating an example operation in accordance with the techniques of the disclosure. For convenience, FIG. 6 is described with respect to FIGS. 1-4. While the operation of FIG. 6 is described with respect to external device 12 and IMD 10 of FIG. 1, in other examples, the operation of FIG. 6 may be performed by, e.g., a remote computing system.

As depicted in FIG. 6, processing circuitry 20 of external device 12 and/or processing circuitry 50 of IMD 10 may receive one or more sensor values indicative of motion of a patient 4 (102). For example, processing circuitry 20 may receive accelerometer data from an accelerometer 36 or from any other one or more sensors 32 for sensing motion. Similarly, processing circuitry 50 may receive accelerometer data from an accelerometer 59 or from any other one or more sensors 58 for sensing motion.

Processing circuitry 20 and/or processing circuitry 50 may determine, based at least in part on the one or more sensor values, an activity level of the patient 4 (104).

Processing circuitry 20 and/or processing circuitry 50 may determine a heart rate threshold for triggering detection of an arrhythmia episode based at least in part on the activity level of the patient 4 (106). In some examples, processing circuitry 20 and/or processing circuitry 50 may, based at least in part on the one or more sensor values, determine whether the activity level of the patient 4 meets or exceeds an activity level threshold. Processing circuitry 20 and/or processing circuitry 50 may, in response to determining that the activity level of the patient 4 meets or exceeds the activity level threshold, determine the heart rate threshold for triggering the arrhythmia episode.

In some examples, processing circuitry 20 and/or processing circuitry 50 may, in response to determining that the activity level of the patient 4 meets or exceeds a first activity level, set the heart rate threshold for triggering detection of the arrhythmia episode to a first heart rate threshold. Processing circuitry 20 and/or processing circuitry 50 may, in response to determining that the activity level of the patient 4 meets or exceeds a second activity level, set the heart rate threshold for triggering detection of the arrhythmia episode to a second heart rate threshold.

In some examples, to set the heart rate threshold to the first heart rate threshold, processing circuitry 20 and/or processing circuitry 50 may determine the first heart rate threshold based at least in part on an age-predicted maximal heart rate for the patient 4 and the activity level of the patient 4. In some examples, to set the heart rate threshold to the second heart rate threshold, processing circuitry 20 and/or processing circuitry 50 may determine the second heart rate threshold based at least in part on the age-predicted maximal heart rate for the patient 4 and the activity level of the patient 4.

In some examples, processing circuitry 20 and/or processing circuitry 50 may determine, based at least in part on the one or more sensor values, whether the activity level for the patient 4 is below a resting threshold for at least a specified period of time. To adjust the heart rate threshold for triggering the arrhythmia episode for the patient 4 based at least in part on the activity level of the patient 4, processing circuitry 20 and/or processing circuitry 50 may, in response to determining that the activity level for the patient 4 is below the resting threshold for at least the specified period of time, adjust the heart rate threshold for triggering the arrhythmia episode.

Processing circuitry 20 and/or processing circuitry 50 may determine whether to trigger the arrhythmia episode for the patient 4 based at least in part on comparing a heart rate of the patient 4 with the heart rate threshold (108). In some examples, to determine whether to trigger the arrhythmia episode for the patient 4, processing circuitry 20 and/or processing circuitry 50 may determine whether the heart rate of the patient is less than or equal to the heart rate threshold. Processing circuitry 20 and/or processing circuitry 50 may, in response to determining that the heart rate of the patient is less than or equal to the heart rate threshold, trigger the arrhythmia episode, where the arrhythmia episode comprises a bradyarrhythmia episode.

In some examples, to determine whether to trigger the arrhythmia episode for the patient, processing circuitry 20 and/or processing circuitry 50 may determine whether the heart rate of the patient 4 is greater than or equal to the heart rate threshold. Processing circuitry 20 and/or processing circuitry 50 may, in response to determining that the heart rate of the patient 4 is greater than or equal to the heart rate threshold, trigger the arrhythmia episode, where the arrhythmia episode comprises a tachyarrhythmia episode.

Processing circuitry 20 and/or processing circuitry 50 may, in response to triggering the arrhythmia episode, collect information associated with the arrhythmia episode (110). In some examples, the information associated with the arrhythmia episode comprise heart rate information of the patient 4 during the arrhythmia episode and a duration of the arrhythmia episode. In some examples, to collect the information associated with the arrhythmia episode, processing circuitry 20 and/or processing circuitry 50 may perform filtering of the heart rate information for motion-type artifacts.

Figure 7:
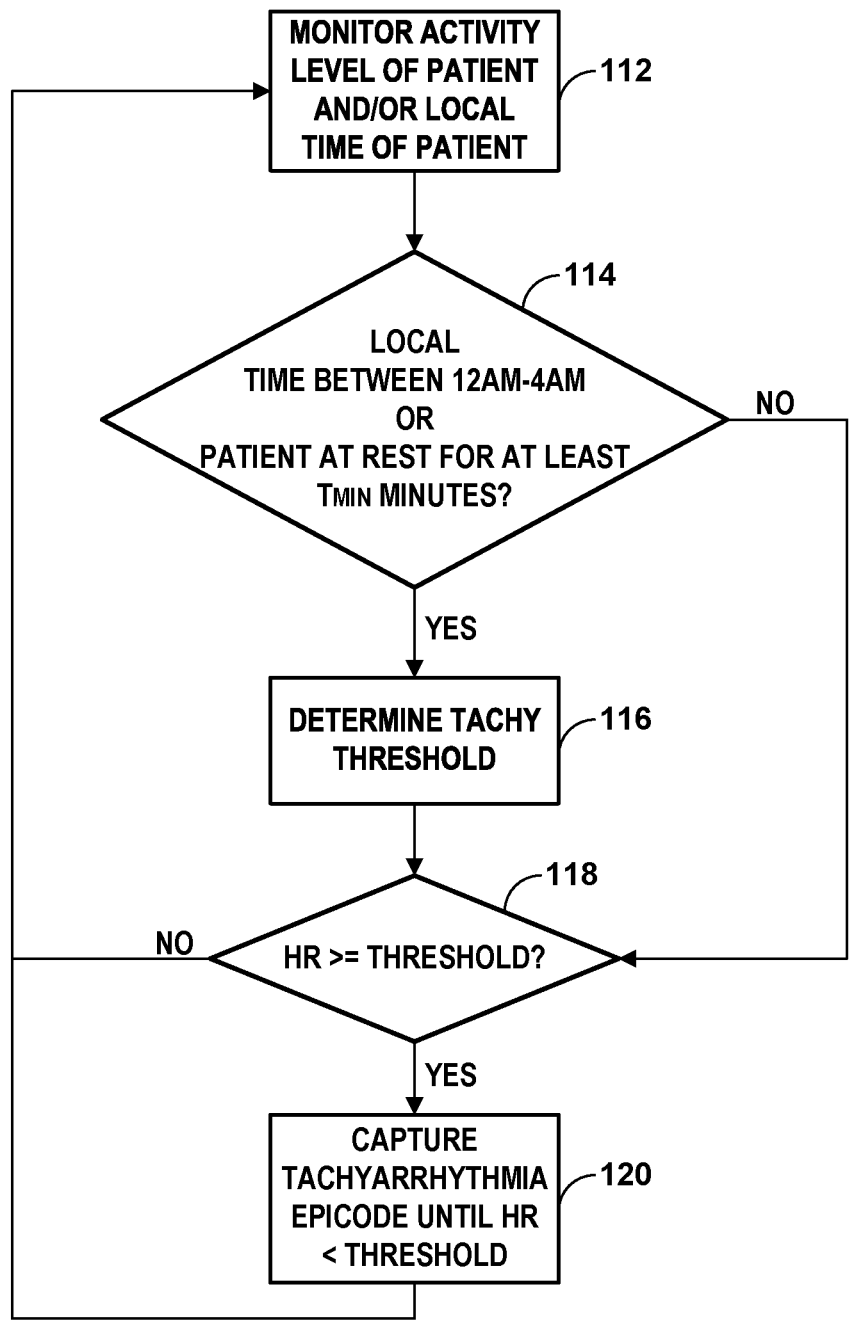
FIG. 7 is a flowchart illustrating an example operation of a medical device in a heart failure monitoring mode in accordance with the techniques of the disclosure.

FIG. 7 is a flowchart illustrating an example operation of a medical device in a heart failure monitoring mode in accordance with the techniques of the disclosure. For convenience, FIG. 7 is described with respect to FIGS. 1-4. In some examples, the operation of FIG. 7 include operations for detecting tachyarrhythmia episodes in patient 4. While the operation of FIG. 7 is described with respect to external device 12 and IMD 10 of FIGS. 1-4, in other examples, the operation of FIG. 7 may be performed by a remote computing system that communicates via a network with external device 12 and/or IMD 10.

As shown in FIG. 7, external device 12 and/or IMD 10 may operate in a heart failure monitoring mode to, for example, monitor a heart failure patient to detect arrhythmia episodes, such as tachyarrhythmia episodes. In heart failure monitoring mode, external device 12 and/or IMD 10 may determine whether patient 4 is at rest and may, in response to determining that patient 4 is at rest, adjust the tachycardia threshold for patient 4.

External device 12 and/or IMD 10 may monitor the activity level of patient 4 and/or the local time of day of patient 4 to determine whether patient 4 is at rest (112). External device 12 and/or IMD 10 may be able to determine whether patient 4 is at rest based at least in part on the activity level of patient 4 sensed by external device 12 and/or IMD 10. For example, if external device 12 and/or IMD 10 determines that the activity intensity of patient 4 is below a certain activity level threshold for a minimum resting duration, external device may determine that patient 4 is at rest. Alternatively, external device 12 and/or IMD 10 may be able to determine whether patient 4 is at rest based at least in part on the time of day. For example, patient 4 is likely to be asleep and therefore at rest in the middle of the night. As such, external device 12 and/or IMD 10 may determine whether patient 4's time of the day is between 12 AM-4 AM or whether patient 4's activity level is below a resting threshold for at least a minimum resting duration $T_{MIN}$ (114).

If external device 12 and/or IMD 10 determines that patient 4's time of the day is between 12 AM-4 AM or that patient 4's activity level is below a resting threshold for at least a minimum resting duration $T_{MIN}$, external device 12 and/or IMD 10 may determine that patient 4 is at rest. External device 12 and/or IMD 10 may, in response, determine the tachycardia threshold for patient 4 (116). Determining the tachycardia threshold may include changing the tachycardia threshold from the current tachycardia threshold to a new tachycardia threshold. For example, external device 12 and/or IMD 10 may set the tachycardia threshold to a specified beats per minute, such as 80 BPM. If external device 12 and/or IMD 10 determines that patient 4 is not at rest, external device 12 and/or IMD 10 may refrain from changing the tachycardia threshold for patient 4 from a default value.

External device 12 and/or IMD 10 may therefore determine whether the heart rate of patient 4 is equal to or larger than the tachycardia threshold (118) and may trigger detection of the tachyarrhythmia episode if the heart rate of patient 4 is equal to or larger than the tachycardia threshold (120). External device 12 and/or IMD 10 may, in response to triggering detection of the tachyarrhythmia episode, capture information associated with detection of the tachyarrhythmia episode until the heart rate of patient 4 is less than the tachycardia threshold. Such information may include the heart rate of patient 4 from onset of the episode until the end of the episode, the duration of the episode, patient 4's cardiac electrogram data during the episode, and the like. After the end of the episode, external device 12 and/or IMD 10 may return to monitoring the activity level of patient 4 and/or the local time of day of patient 4 to determine whether patient 4 is at rest (112).

Figure 8:
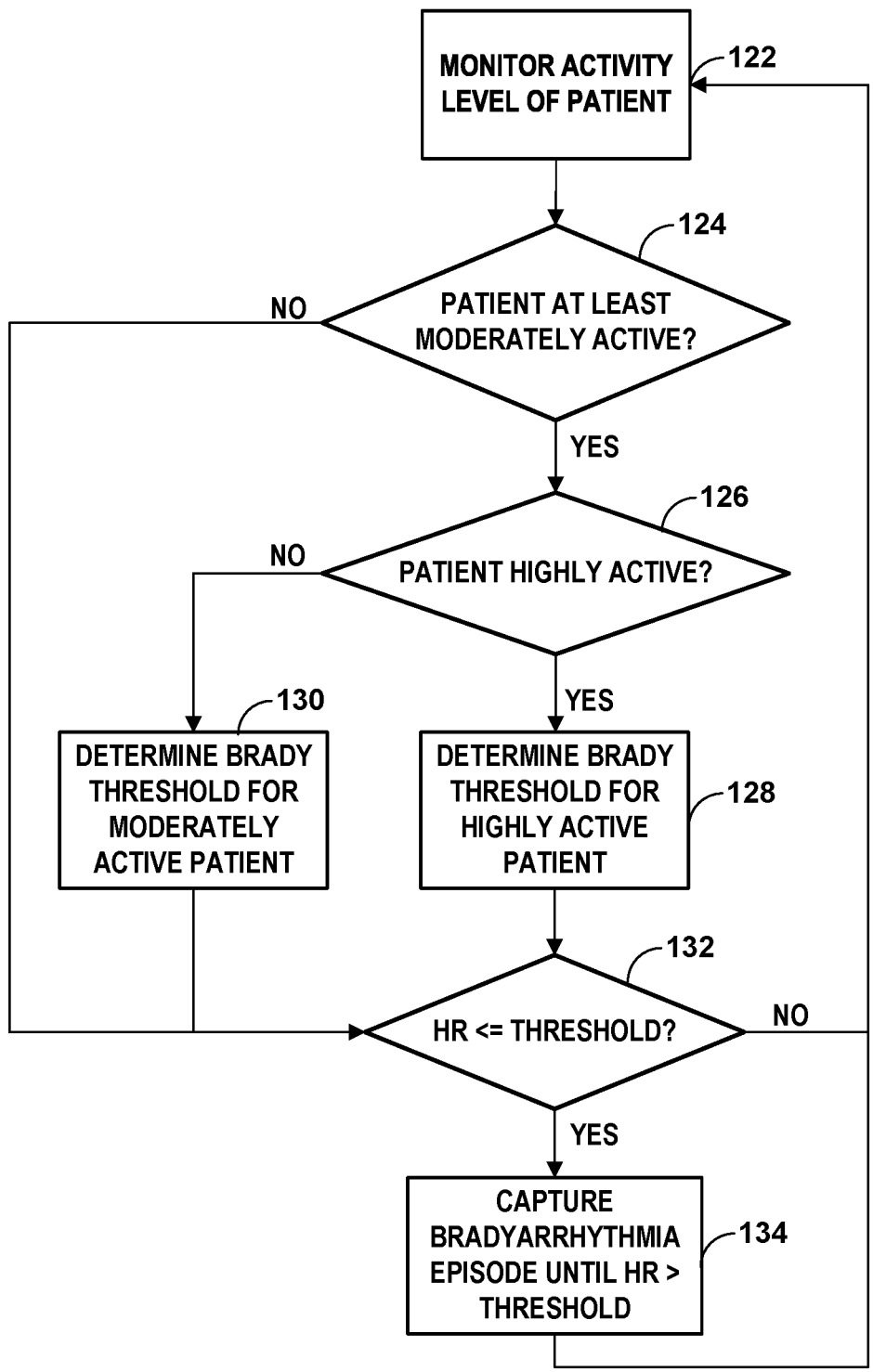
FIG. 8 is a flowchart illustrating an example operation of a medical device in a functional chronotropic incompetence monitoring mode in accordance with the techniques of the disclosure.

FIG. 8 is a flowchart illustrating an example operation of a medical device in a functional chronotropic incompetence monitoring mode in accordance with the techniques of the disclosure. For convenience, FIG. 8 is described with respect to FIGS. 1-4. In some examples, the operation of FIG. 8 include operations for detecting bradyarrhythmia episodes in patient 4. While the operation of FIG. 8 is described with respect to external device 12 and IMD 10 of FIGS. 1-4, in other examples, the operation of FIG. 8 may be performed by a remote computing system that communicates via a network with external device 12 and/or IMD 10.

As shown in FIG. 8, external device 12 and/or IMD 10 may operate in a functional chronotropic incompetence monitoring mode to, for example, monitor a chronotropic incompetence patient to detect arrhythmia episodes, such as bradyarrhythmia episodes. In functional chronotropic incompetence monitoring mode, external device 12 and/or IMD 10 may determine whether patient 4 is at least moderately active and may, in response to determining that patient 4 is at least moderately active, adjust the bradyarrhythmia threshold for patient 4.

More specifically, external device 12 and/or IMD 10 may monitor the activity level of patient 4 based at least in part on sensor values of one or more motion sensors, such as an accelerometer, that senses the motion of patient 4 (122). External device 12 and/or IMD 10 may determine, based on the activity level of patient 4, whether patient 4 is at least moderately active (124). If external device 12 and/or IMD 10 determines that patient 4 is at least moderately active, external device 12 and/or IMD 10 may determine whether patient 4 is highly active based at least in part on sensor values of one or more motion sensors, such as an accelerometer, that senses the motion of patient 4 (126).

For example, external device 12 and/or IMD 10 may determine the bradycardia threshold for patient 4 based at least in part on multiplying an age-predicted maximal heart rate for patient 4 by a weight associated with the activity level of patient 4. Thus, if external device 12 and/or IMD 10 determines that patient 4 is highly active, external device 12 and/or IMD 10 may determine the bradycardia threshold for patient 4 based at least in part on patient 4 being highly active, such as by multiplying the age-predicted maximal heart rate for patient 4 by a weight, such as 0.6, associated with a highly active patient (128). Thus, in the example where patient 4 is 60 years old, the age-predicted maximal heart rate for patient 4 may be 220−60=160, and bradycardia threshold may be 160*0.6=96 BPM.

If external device 12 and/or IMD 10 determines that patient 4 is at least moderately active but not highly active, external device 12 and/or IMD 10 may adjust the bradycardia threshold for patient 4 based at least in part on patient 4 being moderately active, such as by multiplying the age-predicted maximal heart rate for patient 4 by a weight, such as 0.4, associated with a moderately active patient (130). Thus, in the example where patient 4 is 60 years old, the age-predicted maximal heart rate for patient 4 may be 220−60=160, and bradycardia threshold may be 160*0.4=64 BPM. If external device 12 and/or IMD 10 determines that patient 4 is not at least moderately active, external device 12 and/or IMD 10 may refrain from changing the bradycardia threshold for patient 4 from a default bradycardia threshold.

External device 12 and/or IMD 10 may therefore determine whether the heart rate of patient 4 is equal to or less than the bradycardia threshold (132). If external device 12 and/or IMD 10 determines that the heart rate of patient 4 is not equal to or less than the bradycardia threshold, external device 12 and/or IMD 10 may return to monitoring the activity levels of patient 4 (122).

External device 12 and/or IMD 10 and may trigger detection of a bradyarrhythmia episode if the heart rate of patient 4 is equal to or less than the bradycardia threshold (134). External device 12 and/or IMD 10 may, in response to triggering detection of a bradycardia episode, capture information associated with the bradyarrhythmia episode until the heart rate of patient 4 is greater than the bradycardia threshold. Such information may include the heart rate of patient 4 from onset of the episode until the end of the episode, the duration of the episode, patient 4's cardiac electrogram data during the episode, and the like.

In some examples, external device 12 and/or IMD 10 may, while detecting a bradyarrhythmia episode, perform filtering of the heart rate values of patient 4 for noise that may be introduced due to the elevated activity level of patient 4. As such, external device 12 and/or IMD 10 may apply an artificial filter such as a QRS morphology similarity measure to the heart rate values of patient 4 to help ensure that non-artifact episodes are captured. After the end of the episode, external device 12 and/or IMD 10 may return to monitoring the activity levels of patient 4 (122).

The following examples may illustrate one or more aspects of the disclosure.

Example 1

A method comprising: receiving, by processing circuitry, one or more sensor values indicative of motion of a patient; determining, by the processing circuitry and based at least in part on the one or more sensor values, an activity level of the patient; determining, by the processing circuitry, a heart rate threshold for triggering detection of an arrhythmia episode based at least in part on the activity level of the patient; determining, by the processing circuitry, whether to trigger detection of the arrhythmia episode for the patient based at least in part on comparing a heart rate of the patient with the heart rate threshold; and in response to triggering detection of the arrhythmia episode, collecting, by the processing circuitry, information associated with the arrhythmia episode.

Example 2

The method of Example 1, further comprising: determining, by the processing circuitry and based at least in part on the one or more sensor values, whether the activity level of the patient meets or exceeds an activity level threshold; wherein determining the heart rate threshold for triggering detection of the arrhythmia episode comprises in response to determining that the activity level of the patient meets or exceeds the activity level threshold, determining, by the processing circuitry, the heart rate threshold for triggering detection of the arrhythmia episode.

Example 3

The method of Example 2, wherein determining the heart rate threshold for triggering detection of the arrhythmia episode for the patient comprises: in response to determining that the activity level of the patient meets or exceeds a first activity level, setting, by the processing circuitry the heart rate threshold for triggering the arrhythmia episode to a first heart rate threshold; and in response to determining that the activity level of the patient meets or exceeds a second activity level, setting, by the processing circuitry the heart rate threshold for triggering detection of the arrhythmia episode to a second heart rate threshold.

Example 4

The method of Example 3, wherein: setting the heart rate threshold to the first heart rate threshold comprises determining, by the processing circuitry, the first heart rate threshold based at least in part on an age-predicted maximal heart rate for the patient and the activity level of the patient; and setting the heart rate threshold to the second heart rate threshold comprises determining, by the processing circuitry, the second heart rate threshold based at least in part on the age-predicted maximal heart rate for the patient and the activity level of the patient.

Example 5

The method of any of Examples 1-4, wherein determining whether to trigger detection of the arrhythmia episode for the patient comprises: determining, by the processing circuitry, whether the heart rate of the patient is less than or equal to the heart rate threshold; and in response to determining that the heart rate of the patient is less than or equal to the heart rate threshold, triggering, by the processing circuitry, detection of the arrhythmia episode, wherein the arrhythmia episode comprises a bradyarrhythmia episode.

Example 6

The method of any of Examples 1-5, further comprising: determining, by the processing circuitry and based at least in part on the one or more sensor values, whether the activity level for the patient is below a resting threshold for at least a specified period of time; wherein determining the heart rate threshold for triggering detection of the arrhythmia episode for the patient based at least in part on the activity level of the patient comprises in response to determining that the activity level for the patient is below the resting threshold for at least the specified period of time, determining, by the processing circuitry, the heart rate threshold for triggering detection of the arrhythmia episode.

Example 7

The method of Example 6, wherein determining whether to trigger detection of the arrhythmia episode for the patient comprises: determining, by the processing circuitry, whether the heart rate of the patient is greater than or equal to the heart rate threshold; and in response to determining that the heart rate of the patient is greater than or equal to the heart rate threshold, triggering, by the processing circuitry, detection of the arrhythmia episode, wherein the arrhythmia episode comprises a tachyarrhythmia episode.

Example 8

The method of any of Examples 1-7, wherein the information associated with the arrhythmia episode comprise heart rate information of the patient during the arrhythmia episode and a duration of the arrhythmia episode.

Example 9

The method of Example 8, wherein collecting the information associated with the arrhythmia episode comprises: performing, by the processing circuitry, filtering of the information associated with the arrhythmia episode on for motion-type artifacts.

Example 10

The method of any of Examples 1-9, wherein receiving the one or more sensor values indicative of motion of the patient comprises: receiving, by the processing circuitry, accelerometer data from an accelerometer.

Example 11

A medical device comprising: memory; and processing circuitry operably coupled to the memory and configured to: receive one or more sensor values indicative of motion of a patient; determine, based at least in part on the one or more sensor values, an activity level of the patient; determining a heart rate threshold for triggering detection of an arrhythmia episode based at least in part on the activity level of the patient; determine whether to trigger detection of the arrhythmia episode for the patient based at least in part on comparing a heart rate of the patient with the heart rate threshold; and in response to triggering detection of the arrhythmia episode, collect information associated with the arrhythmia episode.

Example 12

The medical device of Example 11, wherein the processing circuitry is further configured to determine, and based at least in part on the one or more sensor values, whether the activity level of the patient meets or exceeds an activity level threshold; and wherein to determine the heart rate threshold for triggering detection of the arrhythmia episode, the processing circuitry is further configured to, in response to determining that the activity level of the patient meets or exceeds the activity level threshold, determine the heart rate threshold for triggering detection the arrhythmia episode.

Example 13

The medical device of Example 12, wherein to determine the heart rate threshold for triggering detection of the arrhythmia episode for the patient, the processing circuitry is further configured to: in response to determining that the activity level of the patient meets or exceeds a first activity level, set the heart rate threshold for triggering detection of the arrhythmia episode to a first heart rate threshold; and in response to determining that the activity level of the patient meets or exceeds a second activity level, set the heart rate threshold for triggering detection the arrhythmia episode to a second heart rate threshold.

Example 14

The medical device of Example 13, wherein: to the heart rate threshold to the first heart rate threshold, the processing circuitry is further configured to determine the first heart rate threshold based at least in part on an age-predicted maximal heart rate for the patient and the activity level of the patient; and to the heart rate threshold to the second heart rate threshold, the processing circuitry is further configured to determine the second heart rate threshold based at least in part on the age-predicted maximal heart rate for the patient and the activity level of the patient.

Example 15

The medical device of any of Examples 11-14, wherein to determine whether to trigger detection of the arrhythmia episode for the patient, the processing circuitry is further configured to: determine whether the heart rate of the patient is less than or equal to the heart rate threshold; and in response to determining that the heart rate of the patient is less than or equal to the heart rate threshold, trigger detection of the arrhythmia episode, wherein the arrhythmia episode comprises a bradyarrhythmia episode.

Example 16

The medical device of any of Examples 11-15, wherein the processing circuitry is further configured to determine, based at least in part on the one or more sensor values, whether the activity level for the patient is below a resting threshold for at least a specified period of time; and wherein to determine the heart rate threshold for triggering detection of the arrhythmia episode for the patient based at least in part on the activity level of the patient, the processing circuitry is further configured to, in response to determining that the activity level for the patient is below the resting threshold for at least the specified period of time, determine the heart rate threshold for triggering detection of the arrhythmia episode.

Example 17

The medical device of Example 16, wherein to determine whether to trigger detection of the arrhythmia episode for the patient, the processing circuitry is further configured to: determine whether the heart rate of the patient is greater than or equal to the heart rate threshold; and in response to determining that the heart rate of the patient is greater than or equal to the heart rate threshold, trigger detection of the arrhythmia episode, wherein the arrhythmia episode comprises a tachyarrhythmia episode.

Example 18

The medical device of any of Examples 11-17, wherein to collect the information associated with the arrhythmia episode, the processing circuitry is further configured to perform filtering of the information associated with the arrhythmia episode for motion-type artifacts.

Example 19

The medical device of any of Examples 11-18, wherein to receive the one or more sensor values indicative of motion of the patient, the processing circuitry is further configured to: receive accelerometer data from an accelerometer.

Example 20

A non-transitory computer-readable medium comprising instructions that, when executed by processing circuitry of a medical device, cause the medical device to: receive one or more sensor values indicative of motion of a patient; determine, based at least in part on the one or more sensor values, an activity level of the patient; determine a heart rate threshold for triggering detection of an arrhythmia episode based at least in part on the activity level of the patient; determine whether to trigger detection of the arrhythmia episode for the patient based at least in part on comparing a heart rate of the patient with the heart rate threshold; and in response to triggering detection of the arrhythmia episode, collect information associated with the arrhythmia episode.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
   receiving, by processing circuitry and from one or more motion sensors, one or more sensor values indicative of motion of a patient;
   determining, by the processing circuitry and based on the one or more sensor values, an activity level of the patient;
   determining, by the processing circuitry, whether the activity level of the patient meets or exceeds an activity level threshold out of a plurality of activity level thresholds;
   in response to determining that the activity level of the patient meets or exceeds the activity level threshold, determining, by the processing circuitry, a heart rate threshold for triggering detection of an arrhythmia episode based at least in part on the activity level of the patient;
   determining, by the processing circuitry, whether to trigger detection of the arrhythmia episode for the patient based at least in part on comparing a heart rate of the patient with the heart rate threshold; and
   in response to triggering detection of the arrhythmia episode, collecting, by the processing circuitry, information associated with the arrhythmia episode.

2. The method of claim 1, wherein determining the heart rate threshold for triggering detection of the arrhythmia episode for the patient comprises:
   in response to determining that the activity level of the patient meets or exceeds a first activity level, setting, by the processing circuitry the heart rate threshold for triggering the arrhythmia episode to a first heart rate threshold; and
   in response to determining that the activity level of the patient meets or exceeds a second activity level, setting, by the processing circuitry the heart rate threshold for triggering detection of the arrhythmia episode to a second heart rate threshold.

3. The method of claim 2, wherein:
   setting the heart rate threshold to the first heart rate threshold comprises determining, by the processing circuitry, the first heart rate threshold based at least in part on an age-predicted maximal heart rate for the patient and the activity level of the patient; and
   setting the heart rate threshold to the second heart rate threshold comprises determining, by the processing circuitry, the second heart rate threshold based at least in part on the age-predicted maximal heart rate for the patient and the activity level of the patient.

4. The method of claim 1, wherein determining whether to trigger detection of the arrhythmia episode for the patient comprises:
   determining, by the processing circuitry, whether the heart rate of the patient is less than or equal to the heart rate threshold; and
   in response to determining that the heart rate of the patient is less than or equal to the heart rate threshold, triggering, by the processing circuitry, detection of the arrhythmia episode, wherein the arrhythmia episode comprises a bradyarrhythmia episode.

5. The method of claim 1, further comprising:
   determining, by the processing circuitry and based at least in part on the one or more sensor values, whether the activity level for the patient is below a resting threshold for at least a specified period of time; and
   wherein determining the heart rate threshold for triggering detection of the arrhythmia episode for the patient based at least in part on the activity level of the patient comprises in response to determining that the activity level for the patient is below the resting threshold for at least the specified period of time, determining, by the processing circuitry, the heart rate threshold for triggering detection of the arrhythmia episode.

6. The method of claim 5, wherein determining whether to trigger detection of the arrhythmia episode for the patient comprises:
   determining, by the processing circuitry, whether the heart rate of the patient is greater than or equal to the heart rate threshold; and
   in response to determining that the heart rate of the patient is greater than or equal to the heart rate threshold, triggering, by the processing circuitry, detection of the arrhythmia episode, wherein the arrhythmia episode comprises a tachyarrhythmia episode.

7. The method of claim 1, wherein the information associated with the arrhythmia episode comprise heart rate information of the patient during the arrhythmia episode and a duration of the arrhythmia episode.

8. The method of claim 7, wherein collecting the information associated with the arrhythmia episode comprises:

performing, by the processing circuitry, filtering of the information associated with the arrhythmia episode on for motion-type artifacts.

9. The method of claim 1, wherein receiving the one or more sensor values indicative of motion of the patient comprises:
receiving, by the processing circuitry, accelerometer data from an accelerometer.

10. A medical device comprising:
memory; and
processing circuitry operably coupled to the memory and configured to:
receive, from one or more motion sensors, one or more sensor values indicative of motion of a patient;
determine, based on the one or more sensor values, an activity level of the patient;
determine whether the activity level of the patient meets or exceeds an activity level threshold out of a plurality of activity level thresholds;
in response to determining that the activity level of the patient meets or exceeds the activity level threshold, determine a heart rate threshold for triggering detection of an arrhythmia episode based at least in part on the activity level of the patient;
determine whether to trigger detection of the arrhythmia episode for the patient based at least in part on comparing a heart rate of the patient with the heart rate threshold; and
in response to triggering detection of the arrhythmia episode, collect information associated with the arrhythmia episode.

11. The medical device of claim 10, wherein to determine the heart rate threshold for triggering detection of the arrhythmia episode for the patient, the processing circuitry is further configured to:
in response to determining that the activity level of the patient meets or exceeds a first activity level, set the heart rate threshold for triggering detection of the arrhythmia episode to a first heart rate threshold; and
in response to determining that the activity level of the patient meets or exceeds a second activity level, set the heart rate threshold for triggering detection the arrhythmia episode to a second heart rate threshold.

12. The medical device of claim 11, wherein:
to the heart rate threshold to the first heart rate threshold, the processing circuitry is further configured to determine the first heart rate threshold based at least in part on an age-predicted maximal heart rate for the patient and the activity level of the patient; and
to the heart rate threshold to the second heart rate threshold, the processing circuitry is further configured to determine the second heart rate threshold based at least in part on the age-predicted maximal heart rate for the patient and the activity level of the patient.

13. The medical device of claim 10, wherein to determine whether to trigger detection of the arrhythmia episode for the patient, the processing circuitry is further configured to:
determine whether the heart rate of the patient is less than or equal to the heart rate threshold; and
in response to determining that the heart rate of the patient is less than or equal to the heart rate threshold, trigger detection of the arrhythmia episode, wherein the arrhythmia episode comprises a bradyarrhythmia episode.

14. The medical device of claim 10, wherein the processing circuitry is further configured to determine, based at least in part on the one or more sensor values, whether the activity level for the patient is below a resting threshold for at least a specified period of time; and
wherein to determine the heart rate threshold for triggering detection of the arrhythmia episode for the patient based at least in part on the activity level of the patient, the processing circuitry is further configured to, in response to determining that the activity level for the patient is below the resting threshold for at least the specified period of time, determine the heart rate threshold for triggering detection of the arrhythmia episode.

15. The medical device of claim 14, wherein to determine whether to trigger detection of the arrhythmia episode for the patient, the processing circuitry is further configured to:
determine whether the heart rate of the patient is greater than or equal to the heart rate threshold; and
in response to determining that the heart rate of the patient is greater than or equal to the heart rate threshold, trigger detection of the arrhythmia episode, wherein the arrhythmia episode comprises a tachyarrhythmia episode.

16. The medical device of claim 10, wherein to collect the information associated with the arrhythmia episode, the processing circuitry is further configured to perform filtering of the information associated with the arrhythmia episode for motion-type artifacts.

17. The medical device of claim 10, wherein to receive the one or more sensor values indicative of motion of the patient, the processing circuitry is further configured to:
receive accelerometer data from an accelerometer.

18. A non-transitory computer-readable medium comprising instructions that, when executed by processing circuitry of a medical device, cause the medical device to:
receive, from one or more motion sensors, one or more sensor values indicative of motion of a patient;
determine, based on the one or more sensor values, an activity level of the patient;
determine a heart rate threshold for triggering detection of an arrhythmia episode based at least in part on the activity level of the patient;
determine whether the activity level of the patient meets or exceeds an activity level threshold out of a plurality of activity level thresholds;
in response to determining that the activity level of the patient meets or exceeds the activity level threshold, determine whether to trigger detection of the arrhythmia episode for the patient based at least in part on comparing a heart rate of the patient with the heart rate threshold; and
in response to triggering detection of the arrhythmia episode, collect information associated with the arrhythmia episode.

* * * * *